US010398358B2

(12) United States Patent
Goel et al.

(10) Patent No.: US 10,398,358 B2
(45) Date of Patent: *Sep. 3, 2019

(54) DYNAMIC SAMPLING

(71) Applicant: NIKE, Inc., Beaverton, OR (US)

(72) Inventors: Manan Goel, Beaverton, OR (US);
Kate Cummings, Seattle, WA (US)

(73) Assignee: NIKE, Inc., Beaverton, OR (US)

( * ) Notice: Subject to any disclaimer, the term of this patent is extended or adjusted under 35 U.S.C. 154(b) by 519 days.

This patent is subject to a terminal disclaimer.

(21) Appl. No.: 14/292,031

(22) Filed: May 30, 2014

(65) Prior Publication Data
US 2014/0358473 A1 Dec. 4, 2014

Related U.S. Application Data

(60) Provisional application No. 61/829,814, filed on May 31, 2013.

(51) Int. Cl.
*A61B 5/11* (2006.01)
*G06F 3/05* (2006.01)
*G01P 1/00* (2006.01)
*G01P 15/00* (2006.01)
*G01D 21/00* (2006.01)
(Continued)

(52) U.S. Cl.
CPC ............. *A61B 5/1118* (2013.01); *G01P 1/00* (2013.01); *G01P 15/00* (2013.01); *G06F 3/05* (2013.01); *A61B 5/0002* (2013.01); *A61B 5/6807* (2013.01); *A61B 5/6831* (2013.01); *A61B 2560/0209* (2013.01);
(Continued)

(58) Field of Classification Search
CPC ........................ A61B 5/118; A61B 2562/0219; A61B 5/681; A63B 24/0062; A63B 24/003; G06F 1/163
See application file for complete search history.

(56) References Cited

U.S. PATENT DOCUMENTS 5,074,302 A * 12/1991 Poore ................. A61N 1/36542
607/19
5,720,769 A * 2/1998 van Oort ............ A61N 1/36542
607/17
(Continued)

FOREIGN PATENT DOCUMENTS

JP 2005352739 A 12/2005
JP 2009039466 A 2/2009
(Continued)

OTHER PUBLICATIONS

Oct. 14, 2014—(WO) ISR App. PCT/US14/040314.

*Primary Examiner* — John E Breene
*Assistant Examiner* — Jeffrey P Aiello
(74) *Attorney, Agent, or Firm* — Banner & Witcoff, Ltd.

(57) ABSTRACT

A wrist-worn athletic performance monitoring system, including an analysis processor, configured to execute an activity recognition processes to recognize a sport or activity being performed by an athlete, and a sampling rate processor, configured to determine a sampling rate at which an analysis processor is to sample data from an accelerometer. The sampling rate processor may determine the sampling rate such that the analysis processor uses a low amount of electrical energy while still being able to carry out an activity classification process to classify an activity being performed.

17 Claims, 10 Drawing Sheets

(51) Int. Cl.
  *G06F 17/40* (2006.01)
  *G06F 19/00* (2018.01)
  *A61B 5/00* (2006.01)

(52) U.S. Cl.
  CPC ...... *A61B 2562/0219* (2013.01); *G01D 21/00* (2013.01); *G06F 17/40* (2013.01); *G06F 19/00* (2013.01)

(56) References Cited

U.S. PATENT DOCUMENTS

| | | | |
|---|---|---|---|
| 7,602,301 B1 * | 10/2009 | Stirling | A61B 5/1127 340/573.1 |
| 7,753,861 B1 * | 7/2010 | Kahn | A61B 5/1118 482/8 |
| 8,760,392 B2 * | 6/2014 | Lloyd | G01P 15/00 345/156 |
| 8,876,738 B1 * | 11/2014 | Kahn | A61B 5/1118 482/8 |
| 9,689,887 B1 | 6/2017 | Srinivas et al. | |
| 9,801,547 B2 * | 10/2017 | Yuen | A61B 5/02405 |
| 9,907,997 B2 * | 3/2018 | Cusey | A63B 24/0062 |
| 2001/0018730 A1 | 8/2001 | Toshitani et al. | |
| 2005/0172311 A1 | 8/2005 | Hjelt et al. | |
| 2007/0293781 A1 | 12/2007 | Sims et al. | |
| 2009/0192556 A1 * | 7/2009 | Wu | A61B 5/0031 607/3 |
| 2009/0319221 A1 | 12/2009 | Kahn et al. | |
| 2010/0120584 A1 | 5/2010 | Oshima et al. | |
| 2011/0254760 A1 | 10/2011 | Lloyd et al. | |
| 2012/0116550 A1 | 5/2012 | Hoffman et al. | |
| 2012/0143093 A1 * | 6/2012 | Stirling | A61B 5/1127 600/592 |
| 2012/0203491 A1 | 8/2012 | Sun et al. | |
| 2013/0158376 A1 * | 6/2013 | Hayter | A61B 5/01 600/347 |
| 2013/0158686 A1 | 6/2013 | Zhang et al. | |
| 2013/0194066 A1 * | 8/2013 | Rahman | G05B 1/01 340/5.51 |
| 2013/0217979 A1 | 8/2013 | Blackadar et al. | |
| 2014/0172341 A1 * | 6/2014 | Vandersleen | G01N 27/3273 702/89 |
| 2014/0267799 A1 * | 9/2014 | Sadasivam | H04N 5/23216 348/207.99 |
| 2014/0288876 A1 * | 9/2014 | Donaldson | A61B 5/1118 702/141 |
| 2014/0358472 A1 * | 12/2014 | Goel | A61B 5/1118 702/141 |

FOREIGN PATENT DOCUMENTS

| | | |
|---|---|---|
| JP | 2011525414 A | 9/2011 |
| WO | 2011032016 A1 | 3/2011 |

* cited by examiner

DYNAMIC SAMPLING

CROSS REFERENCE TO RELATED APPLICATIONS

This application claims the benefit of, and priority to, U.S. Provisional Patent Application No. 61/829,814, entitled "DYNAMIC SAMPLING" filed May 31, 2013. The content of which is expressly incorporated herein by reference in its entirety for any and all non-limiting purposes.

BACKGROUND

Modern technology has given rise to a wide variety of different electronic and/or communication devices that keep users in touch with one another, entertained, and informed. A wide variety of portable electronic devices are available for these purposes, such as: cellular telephones; personal digital assistants ("PDAs"); pagers; beepers; MP3 or other audio playback devices; radios; portable televisions, DVD players, or other video playing devices; watches; GPS systems; etc. Many people like to carry one or more of these types of devices with them when they exercise and/or participate in athletic events, for example, to keep them in contact with others (e.g., in case of inclement weather, injuries; or emergencies; to contact coaches or trainers; etc.), to keep them entertained, to provide information (time, direction, location, and the like).

Athletic performance monitoring systems also have benefited from recent advancements in electronic device and digital technology. Electronic performance monitoring devices allow for monitoring of many physical or physiological characteristics associated with exercise or other athletic performances, including, for example: speed and distance data, altitude data, GPS data, heart rate, pulse rate, blood pressure data, body temperature, etc. Specifically, these athletic performance monitoring systems have benefited from recent advancements in microprocessor design, allowing increasingly complex computations and processes to be executed by microprocessors of successively diminutive size. These modern microprocessors may be used for execution of activity recognition processes, such that a sport or activity that is being carried out by an athlete can be recognized, and information related to that sport or activity can be analyzed and/or stored. However, these systems are often powered by limited power sources, such as rechargeable batteries, such that a device may be worn by an athlete to allow for portable activity monitoring and recognition. As the computations carried out by athletic performance monitoring systems have become increasingly complex, the power consumption of the integral microprocessors carrying out the computations has increased significantly. Consequently, the usable time between battery recharges has decreased. Accordingly, there is a need for more efficient systems and methods for prolonging the battery life of athletic performance monitoring systems. Further, certain systems are not configured to permit the accurate capture of intense fitness activity.

Aspects of this disclosure are directed towards novel systems and methods that address one or more of these deficiencies. Further aspects relate to minimizing other shortcomings in the art

SUMMARY

The following presents a simplified summary of the present disclosure in order to provide a basic understanding of some aspects of the invention. This summary is not an extensive overview of the invention. It is not intended to identify key or critical elements of the invention or to delineate the scope of the invention. The following summary merely presents some concepts of the invention in a simplified form as a prelude to the more detailed description provided below.

Aspects of the systems and methods described herein relate non-transitory computer-readable media with computer-executable instructions for receiving user movement data into a sampling rate processor on a sensor device. The movement data may be received from an accelerometer on the device, wherein the device is positioned on an appendage of a user, and is sampling from the accelerometer at a first sampling rate. Further, the received acceleration data may be classified into an activity category that represents an activity being performed by the user, and based on this classification, a second sampling rate may be selected for receiving data from the accelerometer or other sensor(s).

In another aspect, this disclosure relates to an apparatus configured to be worn on an appendage of a user, including a power supply, and a sensor configured to capture data (such as for example acceleration data) based on the user's movement. The apparatus may further include an analysis processor, and a sampling rate processor. In one embodiment, the sampling rate processor determines a first sampling rate to sample the acceleration data such that power consumption by the analysis processor is reduced. The apparatus may further attempt to classify the data sampled at the first sampling rate into an activity category.

In yet another aspect, this disclosure relates to non-transitory computer-readable media with computer-executable instructions that when executed by a processor is configured to receive data from a sensor (such as for example, acceleration data from an accelerometer), identify or select an activity from the data, and adjust the sampling rate of the sensor based on the identified activity. Further sampling rates, such as for other sensors, may be adjusted based upon the identified activity and/or movements of the user.

This Summary is provided to introduce a selection of concepts in a simplified form that are further described below in the Detailed Description. The Summary is not intended to identify key features or essential features of the claimed subject matter, nor is it intended to be used to limit the scope of the claimed subject matter.

DETAILED DESCRIPTION

Aspects of this disclosure involve obtaining, storing, and/or processing athletic data relating to the physical movements of an athlete. The athletic data may be actively or passively sensed and/or stored in one or more non-transitory storage mediums. Still further aspects relate to using athletic data to generate an output, such as for example, calculated athletic attributes, feedback signals to provide guidance, and/or other information. These, and other aspects, will be discussed in the context of the following illustrative examples of a personal training system.

In the following description of the various embodiments, reference is made to the accompanying drawings, which form a part hereof, and in which is shown by way of illustration various embodiments in which aspects of the disclosure may be practiced. It is to be understood that other embodiments may be utilized and structural and functional modifications may be made without departing from the scope and spirit of the present disclosure. Further, headings within this disclosure should not be considered as limiting aspects of the disclosure and the example embodiments are not limited to the example headings.

I. Example Personal Training System

A. Illustrative Networks

Figure 1:
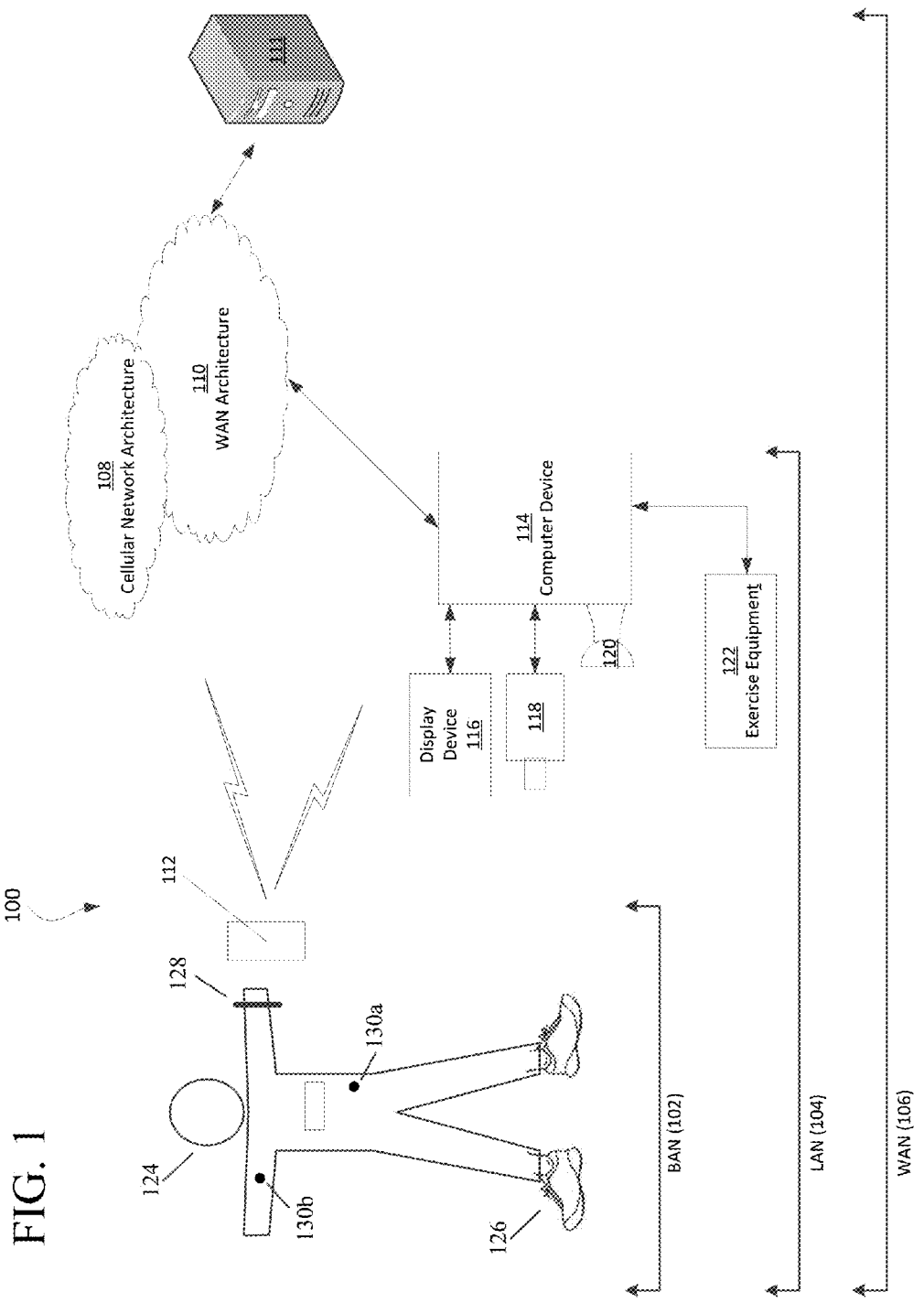
FIG. 1 illustrates an example system that may be configured to provide personal training and/or obtain data from the physical movements of a user in accordance with example embodiments.

Aspects of this disclosure relate to systems and methods that may be utilized across a plurality of networks. In this regard, certain embodiments may be configured to adapt to dynamic network environments. Further embodiments may be operable in differing discrete network environments. FIG. 1 illustrates an example of a personal training system 100 in accordance with example embodiments. Example system 100 may include one or more interconnected networks, such as the illustrative body area network (BAN) 102, local area network (LAN) 104, and wide area network (WAN) 106. As shown in FIG. 1 (and described throughout this disclosure), one or more networks (e.g., BAN 102, LAN 104, and/or WAN 106), may overlap or otherwise be inclusive of each other. Those skilled in the art will appreciate that the illustrative networks 102-106 are logical networks that may each comprise one or more different communication protocols and/or network architectures and yet may be configured to have gateways to each other or other networks. For example, each of BAN 102, LAN 104 and/or WAN 106 may be operatively connected to the same physical network architecture, such as cellular network architecture 108 and/or WAN architecture 110. For example, portable electronic device 112, which may be considered a component of both BAN 102 and LAN 104, may comprise a network adapter or network interface card (NIC) configured to translate data and control signals into and from network messages according to one or more communication protocols, such as the Transmission Control Protocol (TCP), the Internet Protocol (IP), and the User Datagram Protocol (UDP) through one or more of architectures 108 and/or 110. These protocols are well known in the art, and thus will not be discussed here in more detail.

Network architectures 108 and 110 may include one or more information distribution network(s), of any type(s) or topology(s), alone or in combination(s), such as for example, cable, fiber, satellite, telephone, cellular, wireless, etc. and as such, may be variously configured such as having one or more wired or wireless communication channels (including but not limited to: WIFI®, BLUETOOTH®, Near-Field Communication (NFC) and/or ANT technologies). Thus, any device within a network of FIG. 1, (such as portable electronic device 112 or any other device described herein) may be considered inclusive to one or more of the different logical networks 102-106. With the foregoing in mind, example components of an illustrative BAN and LAN (which may be coupled to WAN 106) will be described.

1. Example Local Area Network

LAN 104 may include one or more electronic devices, such as for example, computer device 114. Computer device 114, or any other component of system 100, may comprise a mobile terminal, such as a telephone, music player, tablet, netbook or any portable device. In other embodiments, computer device 114 may comprise a media player or recorder, desktop computer, server(s), a gaming console, such as for example, a MICROSOFT® XBOX, SONY® PLAYSTATION, and/or a NINTENDO® WII gaming consoles. Those skilled in the art will appreciate that these are merely example devices for descriptive purposes and this disclosure is not limited to any console or computing device.

Those skilled in the art will appreciate that the design and structure of computer device 114 may vary depending on several factors, such as its intended purpose. One example implementation of computer device 114 is provided in FIG. 2, which illustrates a block diagram of computing device 200. Those skilled in the art will appreciate that the disclosure of FIG. 2 may be applicable to any device disclosed herein. Device 200 may include one or more processors, such as processor 202-1 and 202-2 (generally referred to herein as "processors 202" or "processor 202"). Processors 202 may communicate with each other or other components via an interconnection network or bus 204. Processor 202 may include one or more processing cores, such as cores 206-1 and 206-2 (referred to herein as "cores 206" or more generally as "core 206"), which may be implemented on a single integrated circuit (IC) chip.

Cores 206 may comprise a shared cache 208 and/or a private cache (e.g., caches 210-1 and 210-2, respectively). One or more caches 208/210-1 may locally cache data stored in a system memory, such as memory 212, for faster access by components of the processor 202. Memory 212 may be in communication with the processors 202 via a chipset 216. Cache 208 may be part of system memory 212 in certain embodiments. Memory 212 may include, but is not limited to, random access memory (RAM), read only memory (ROM), and include one or more of solid-state memory, optical or magnetic storage, and/or any other medium that can be used to store electronic information. Yet other embodiments may omit system memory 212.

System 200 may include one or more I/O devices (e.g., I/O devices 214-1 through 214-3, each generally referred to as I/O device 214). I/O data from one or more I/O devices 214 may be stored at one or more caches 208, 210-1 and/or system memory 212. Each of I/O devices 214 may be permanently or temporarily configured to be in operative communication with a component of system 100 using any physical or wireless communication protocol.

Returning to FIG. 1, four example I/O devices (shown as elements 116-122) are shown as being in communication with computer device 114. Those skilled in the art will appreciate that one or more of devices 116-122 may be stand-alone devices or may be associated with another device besides computer device 114. For example, one or more I/O devices may be associated with or interact with a component of BAN 102 and/or WAN 106. I/O devices 116-122 may include, but are not limited to athletic data acquisition units, such as for example, sensors. One or more I/O devices may be configured to sense, detect, and/or measure an athletic parameter from a user, such as user 124. Examples include, but are not limited to: an accelerometer, a gyroscope, a location-determining device (e.g., GPS), light (including non-visible light) sensor, temperature sensor (including ambient temperature and/or body temperature), sleep pattern sensors, heart rate monitor, image-capturing sensor, moisture sensor, force sensor, compass, angular rate sensor, and/or combinations thereof among others.

In further embodiments, I/O devices 116-122 may be used to provide an output (e.g., audible, visual, or tactile cue) and/or receive an input, such as a user input from athlete 124. Example uses for these illustrative I/O devices are provided below, however, those skilled in the art will appreciate that such discussions are merely descriptive of some of the many options within the scope of this disclosure. Further, reference to any data acquisition unit, I/O device, or sensor is to be interpreted disclosing an embodiment that may have one or more I/O device, data acquisition unit, and/or sensor disclosed herein or known in the art (either individually or in combination).

Information from one or more devices (across one or more networks) may be used (or be utilized in the formation of) a variety of different parameters, metrics or physiological characteristics including but not limited to: motion parameters, or motion data, such as speed, acceleration, distance, steps taken, direction, relative movement of certain body portions or objects to others, or other motion parameters which may be expressed as angular rates, rectilinear rates or combinations thereof, physiological parameters, such as calories, heart rate, sweat detection, effort, oxygen consumed, oxygen kinetics, and other metrics which may fall within one or more categories, such as: pressure, impact forces, information regarding the athlete, such as height, weight, age, demographic information and combinations thereof.

System 100 may be configured to transmit and/or receive athletic data, including the parameters, metrics, or physiological characteristics collected within system 100 or otherwise provided to system 100. As one example, WAN 106 may comprise sever 111. Server 111 may have one or more components of system 200 of FIG. 2. In one embodiment, server 111 comprises at least a processor and a memory, such as processor 206 and memory 212. Server 111 may be configured to store computer-executable instructions on a non-transitory computer-readable medium. The instructions may comprise athletic data, such as raw or processed data collected within system 100. System 100 may be configured to transmit data, such as energy expenditure points, to a social networking website or host such a site. Server 111 may be utilized to permit one or more users to access and/or compare athletic data. As such, server 111 may be configured to transmit and/or receive notifications based upon athletic data or other information.

Returning to LAN 104, computer device 114 is shown in operative communication with a display device 116, an image-capturing device 118, sensor 120 and exercise device 122, which are discussed in turn below with reference to example embodiments. In one embodiment, display device 116 may provide audio-visual cues to athlete 124 to perform a specific athletic movement. The audio-visual cues may be provided in response to computer-executable instruction executed on computer device 114 or any other device, including a device of BAN 102 and/or WAN. Display device 116 may be a touchscreen device or otherwise configured to receive a user-input.

In one embodiment, data may be obtained from image-capturing device 118 and/or other sensors, such as sensor 120, which may be used to detect (and/or measure) athletic parameters, either alone or in combination with other devices, or stored information. Image-capturing device 118 and/or sensor 120 may comprise a transceiver device. In one embodiment sensor 120 may comprise an infrared (IR), electromagnetic (EM) or acoustic transceiver. For example, image-capturing device 118, and/or sensor 120 may transmit waveforms into the environment, including towards the direction of athlete 124 and receive a "reflection" or otherwise detect alterations of those released waveforms. Those skilled in the art will readily appreciate that signals corresponding to a multitude of different data spectrums may be utilized in accordance with various embodiments. In this regard, image-capturing devices 118 and/or sensor 120 may detect waveforms emitted from external sources (e.g., not system 100). For example, image-capturing devices 118 and/or sensor 120 may detect heat being emitted from user 124 and/or the surrounding environment. Thus, image-capturing device 118 and/or sensor 120 may comprise one or more thermal imaging devices. In one embodiment, image-capturing device 118 and/or sensor 120 may comprise an IR device configured to perform range phenomenology.

In one embodiment, exercise device 122 may be any device configurable to permit or facilitate the athlete 124 performing a physical movement, such as for example a treadmill, step machine, etc. There is no requirement that the device be stationary. In this regard, wireless technologies permit portable devices to be utilized, thus a bicycle or other mobile exercising device may be utilized in accordance with certain embodiments. Those skilled in the art will appreciate that equipment 122 may be or comprise an interface for receiving an electronic device containing athletic data performed remotely from computer device 114. For example, a user may use a sporting device (described below in relation to BAN 102) and upon returning home or the location of equipment 122, download athletic data into element 122 or any other device of system 100. Any I/O device disclosed herein may be configured to receive activity data.

2. Body Area Network

BAN 102 may include two or more devices configured to receive, transmit, or otherwise facilitate the collection of athletic data (including passive devices). Exemplary devices may include one or more data acquisition units, sensors, or devices known in the art or disclosed herein, including but not limited to display device 116, image-capturing device 118, sensor 120, and excercise device 122. Two or more components of BAN 102 may communicate directly, yet in other embodiments, communication may be conducted via a third device, which may be part of BAN 102, LAN 104, and/or WAN 106. One or more components of LAN 104 or WAN 106 may form part of BAN 102. In certain implementations, whether a device, such as portable device 112, is part of BAN 102, LAN 104, and/or WAN 106, may depend on the athlete's proximity to an access points permit communication with mobile cellular network architecture 108 and/or WAN architecture 110. User activity and/or preference may also influence whether one or more components are utilized as part of BAN 102. Example embodiments are provided below.

User 124 may be associated with (e.g., possess, carry, wear, and/or interact with) any number of devices, such as portable device 112, shoe-mounted device 126, wrist-worn device 128 and/or a sensing location, such as sensing location 130, which may comprise a physical device or a location that is used to collect information. One or more of portable device 112, shoe-mounted device 126, wrist-worn device 128, and/or sensing locations 130a and 130b may not be specially designed for fitness or athletic purposes. Indeed, aspects of this disclosure relate to utilizing data from a plurality of devices, some of which are not fitness devices, to collect, detect, and/or measure athletic data. In certain embodiments, one or more devices of BAN 102 (or any other network) may comprise a fitness or sporting device that is specifically designed for a particular sporting use. As used herein, the term "sporting device" includes any physical object that may be used or implicated during a specific sport or fitness activity. Exemplary sporting devices may include, but are not limited to: golf balls, basketballs, baseballs, soccer balls, footballs, powerballs, hockey pucks, weights, bats, clubs, sticks, paddles, mats, and combinations thereof. In further embodiments, exemplary fitness devices may include objects within a sporting environment where a specific sport occurs, including the environment itself, such as a goal net, hoop, backboard, portions of a field, such as a midline, outer boundary marker, base, and combinations thereof.

In this regard, those skilled in the art will appreciate that one or more sporting devices may also be part of (or form) a structure and vice-versa, a structure may comprise one or more sporting devices or be configured to interact with a sporting device. For example, a first structure may comprise a basketball hoop and a backboard, which may be removable and replaced with a goal post. In this regard, one or more sporting devices may comprise one or more sensors, such one or more of the sensors discussed above in relation to FIGS. 1-3, that may provide information utilized, either independently or in conjunction with other sensors, such as one or more sensors associated with one or more structures. For example, a backboard may comprise a first sensors configured to measure a force and a direction of the force by a basketball upon the backboard and the hoop may comprise a second sensor to detect a force. Similarly, a golf club may comprise a first sensor configured to detect grip attributes on the shaft and a second sensor configured to measure impact with a golf ball.

Looking to the illustrative portable device 112, it may be a multi-purpose electronic device, that for example, includes a telephone or digital music player, including an IPOD®, IPAD®, or IPHONE®, brand devices available from APPLE®, Inc. of Cupertino, Calif. or ZUNE® or MICROSOFT® WINDOWS devices available from MICROSOFT® of Redmond, Wash. As known in the art, digital media players can serve as an output device, input device, and/or storage device for a computer. Device 112 may be configured as an input device for receiving raw or processed data collected from one or more devices in BAN 102, LAN 104, or WAN 106. In one or more embodiments, portable device 112 may comprise one or more components of computer device 114. For example, portable device 112 may be include a display 116, image-capturing device 118, and/or one or more data acquisition devices, such as any of display device 116, image-capturing device 118, sensor 120, and exercise device 122 discussed above, with or without additional components, so as to comprise a mobile terminal.

a. Illustrative Apparel/Accessory Sensors

In certain embodiments, I/O devices may be formed within or otherwise associated with user's 124 clothing or accessories, including a watch, armband, wristband, necklace, shirt, shoe, or the like. These devices may be configured to monitor athletic movements of a user. It is to be understood that they may detect athletic movement during user's 124 interactions with computer device 114 and/or operate independently of computer device 114 (or any other device disclosed herein). For example, one or more devices in BAN 102 may be configured to function as an-all day activity monitor that measures activity regardless of the user's proximity or interactions with computer device 114. It is to be further understood that the sensory system 302 shown in FIG. 3 and the device assembly 400 shown in FIG. 4, each of which are described in the following paragraphs, are merely illustrative examples.

i. Shoe-Mounted Device

Figure 3:
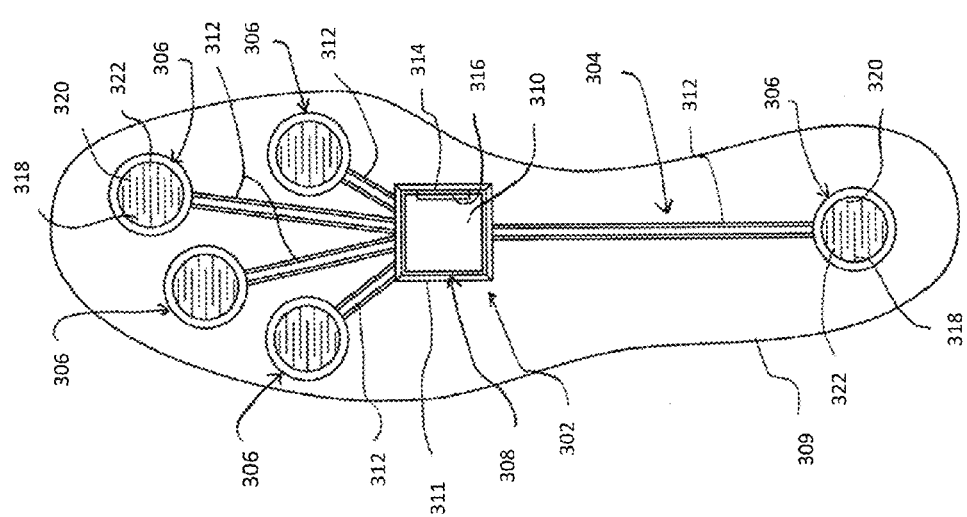
FIG. 3 shows an illustrative sensor assembly that may be worn by a user in accordance with example embodiments.

In certain embodiments, shoe-mounted device 126 shown in FIG. 1, may comprise footwear which may include one or more sensors, including but not limited to those disclosed herein and/or known in the art. FIG. 3 illustrates one example embodiment of a sensor system 302 providing one or more sensor assemblies 304. Assembly 304 may comprise one or more sensors, such as for example, an accelerometer, gyroscope, location-determining components, force sensors and/or or any other sensor disclosed herein or known in the art. In the illustrated embodiment, assembly 304 incorporates a plurality of sensors, which may include force-sensitive resistor (FSR) sensors 306; however, other sensor(s) may be utilized. Port 308 may be positioned within a sole structure 309 of a shoe, and is generally configured for communication with one or more electronic devices. Port 308 may optionally be provided to be in communication with an electronic module 310, and the sole structure 309 may optionally include a housing 311 or other structure to receive the module 310. The sensor system 302 may also include a plurality of leads 312 connecting the FSR sensors 306 to the port 308, to enable communication with the module 310 and/or another electronic device through the port 308. Module 310 may be contained within a well or cavity in a sole structure of a shoe, and the housing 311 may be positioned within the well or cavity. In one embodiment, at least one gyroscope and at least one accelerometer are provided within a single housing, such as module 310 and/or housing 311. In at least a further embodiment, one or more sensors are provided that, when operational, are configured to provide directional information and angular rate data. The port 308 and the module 310 include complementary interfaces 314, 316 for connection and communication.

In certain embodiments, at least one force-sensitive resistor 306 shown in FIG. 3 may contain first and second electrodes or electrical contacts 318, 320 and a force-sensitive resistive material 322 disposed between the electrodes 318, 320 to electrically connect the electrodes 318, 320 together. When pressure is applied to the force-sensitive material 322, the resistivity and/or conductivity of the force-sensitive material 322 changes, which changes the electrical potential between the electrodes 318, 320. The change in resistance can be detected by the sensor system 302 to detect the force applied on the sensor 316. The force-sensitive resistive material 322 may change its resistance under pressure in a variety of ways. For example, the force-sensitive material 322 may have an internal resistance that decreases when the material is compressed. Further embodiments may utilize "volume-based resistance" may be measured, which may be implemented through "smart materials." As another example, the material 322 may change the resistance by changing the degree of surface-to-surface contact, such as between two pieces of the force sensitive material 322 or between the force sensitive material 322 and one or both electrodes 318, 320. In some circumstances, this type of force-sensitive resistive behavior may be described as "contact-based resistance."

ii. Wrist-Worn Device

Figure 4:
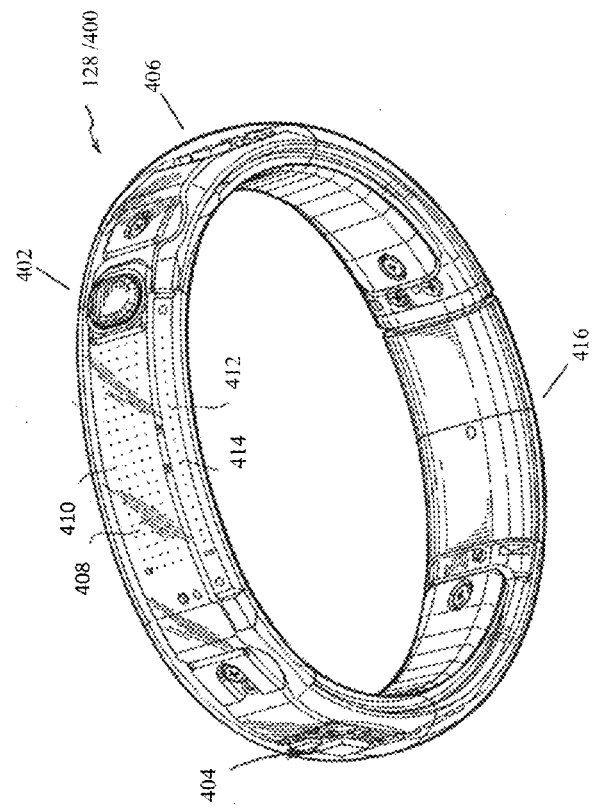
FIG. 4 shows another example sensor assembly that may be worn by a user in accordance with example embodiments.

As shown in FIG. 4, device 400 (which may resemble or comprise wrist-worn device 128 shown in FIG. 1), may be configured to be worn by user 124, such as around a wrist, arm, ankle, neck or the like. Device 400 may include an input mechanism, such as a depressible input button 402 configured to be used during operation of the device 400. The input button 402 may be operably connected to a controller 404 and/or any other electronic components, such as one or more of the elements discussed in relation to computer device 114 shown in FIG. 1. Controller 404 may be embedded or otherwise part of housing 406. Housing 406 may be formed of one or more materials, including elastomeric components and comprise one or more displays, such as display 408. The display may be considered an illuminable portion of the device 400. The display 408 may include a series of individual lighting elements or light members such as LED lights 410. The lights may be formed in an array and operably connected to the controller 404. Device 400 may include an indicator system 412, which may also be considered a portion or component of the overall display 408. Indicator system 412 can operate and illuminate in conjunction with the display 408 (which may have pixel member 414) or completely separate from the display 408. The indicator system 412 may also include a plurality of additional lighting elements or light members, which may also take the form of LED lights in an exemplary embodiment. In certain embodiments, indicator system may provide a visual indication of goals, such as by illuminating a portion of lighting members of indicator system 412 to represent accomplishment towards one or more goals. Device 400 may be configured to display data expressed in terms of activity points or currency earned by the user based on the activity of the user, either through display 408 and/or indicator system 412.

A fastening mechanism 416 can be disengaged wherein the device 400 can be positioned around a wrist or portion of the user 124 and the fastening mechanism 416 can be subsequently placed in an engaged position. In one embodiment, fastening mechanism 416 may comprise an interface, including but not limited to a USB port, for operative interaction with computer device 114 and/or devices, such as sensor 120 and/or device 112. In certain embodiments, fastening member may comprise one or more magnets. In one embodiment, fastening member may be devoid of moving parts and rely entirely on magnetic forces.

In certain embodiments, device 400 may comprise a sensor assembly (not shown in FIG. 4). The sensor assembly may comprise a plurality of different sensors, including those disclosed herein and/or known in the art. In an example embodiment, the sensor assembly may comprise or permit operative connection to any sensor disclosed herein or known in the art. Device 400 and or its sensor assembly may be configured to receive data obtained from one or more external sensors.

iii. Apparel and/or Body Location Sensing

Elements 130a and 130b of FIG. 1 shows an example sensory location which may be associated with a physical apparatus, such as a sensor, data acquisition unit, or other device. Yet in other embodiments, it may be a specific location of a body portion or region that is monitored, such as via an image capturing device (e.g., image-capturing device 118). In certain embodiments, elements 130a and 130b may comprise a sensor, such that elements 130a and 130b may be sensors integrated into apparel, such as athletic clothing. Such sensors may be placed at any desired location of the body of user 124. Sensors 130a/b may communicate (e.g., wirelessly) with one or more devices (including other sensors) of BAN 102, LAN 104, and/or WAN 106. In certain embodiments, passive sensing surfaces may reflect waveforms, such as infrared light, emitted by image-capturing device 118 and/or sensor 120. In one embodiment, passive sensors located on user's 124 apparel may comprise generally spherical structures made of glass or other transparent or translucent surfaces which may reflect waveforms. Different classes of apparel may be utilized in which a given class of apparel has specific sensors configured to be located proximate to a specific portion of the user's 124 body when properly worn. For example, golf apparel may include one or more sensors positioned on the apparel in a first configuration and yet soccer apparel may include one or more sensors positioned on apparel in a second configuration.

Figure 5:
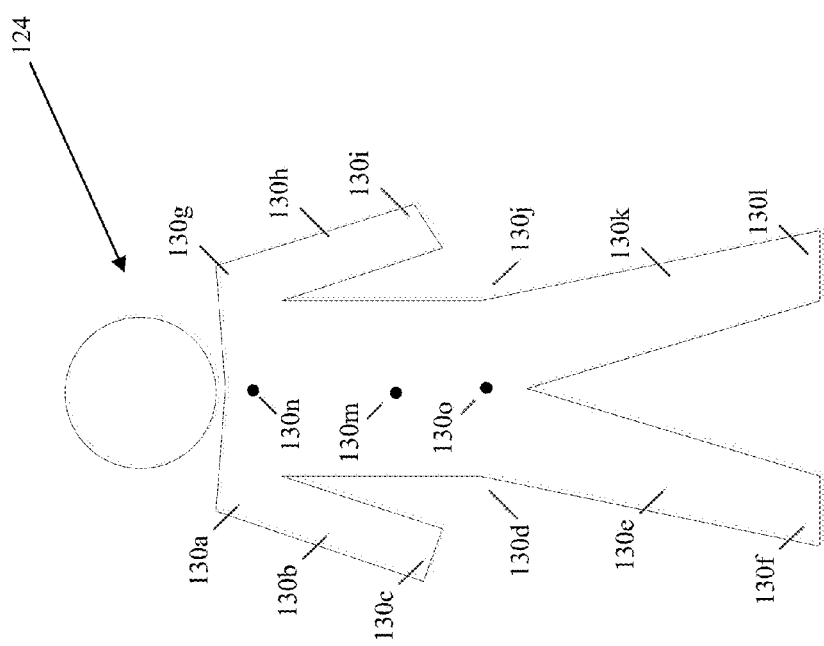
FIG. 5 shows illustrative locations for sensory input which may include physical sensors located on/in a user's clothing and/or be based upon identification of relationships between two moving body parts of the user.

FIG. 5 shows illustrative locations for sensory input (see, e.g., sensory locations 130a-130o). In this regard, sensors may be physical sensors located on/in a user's clothing, yet in other embodiments, sensor locations 130a-130o may be based upon identification of relationships between two moving body parts. For example, sensor location 130a may be determined by identifying motions of user 124 with an image-capturing device, such as image-capturing device 118. Thus, in certain embodiments, a sensor may not physically be located at a specific location (such as one or more of sensor locations 130a-130o), but is configured to sense properties of that location, such as with image-capturing device 118 or other sensor data gathered from other locations. In this regard, the overall shape or portion of a user's body may permit identification of certain body parts. Regardless of whether an image-capturing device is utilized and/or a physical sensor located on the user 124, and/or using data from other devices, (such as sensory system 302), device assembly 400 and/or any other device or sensor disclosed herein or known in the art is utilized, the sensors may sense a current location of a body part and/or track movement of the body part. In one embodiment, sensory data relating to location 130m may be utilized in a determination of the user's center of gravity (a.k.a, center of mass). For example, relationships between location 130a and location(s) 130f/130l with respect to one or more of location(s) 130m-130o may be utilized to determine if a user's center of gravity has been elevated along the vertical axis (such as during a jump) or if a user is attempting to "fake" a jump by bending and flexing their knees. In one embodiment, sensor location 130n may be located at about the sternum of user 124. Likewise, sensor location 130o may be located approximate to the naval of user 124. In certain embodiments, data from sensor locations 130m-130o may be utilized (alone or in combination with other data) to determine the center of gravity for user 124. In further embodiments, relationships between multiple several sensor locations, such as sensors 130m-130o, may be utilized in determining orientation of the user 124 and/or rotational forces, such as twisting of user's 124 torso. Further, one or more locations, such as location(s), may be utilized to as a center of moment location. For example, in one embodiment, one or more of location(s) 130m-130o may serve as a point for a center of moment location of user 124. In another embodiment, one or more body locations may serve as a center of moment of specific body parts or regions.

Figure 6:
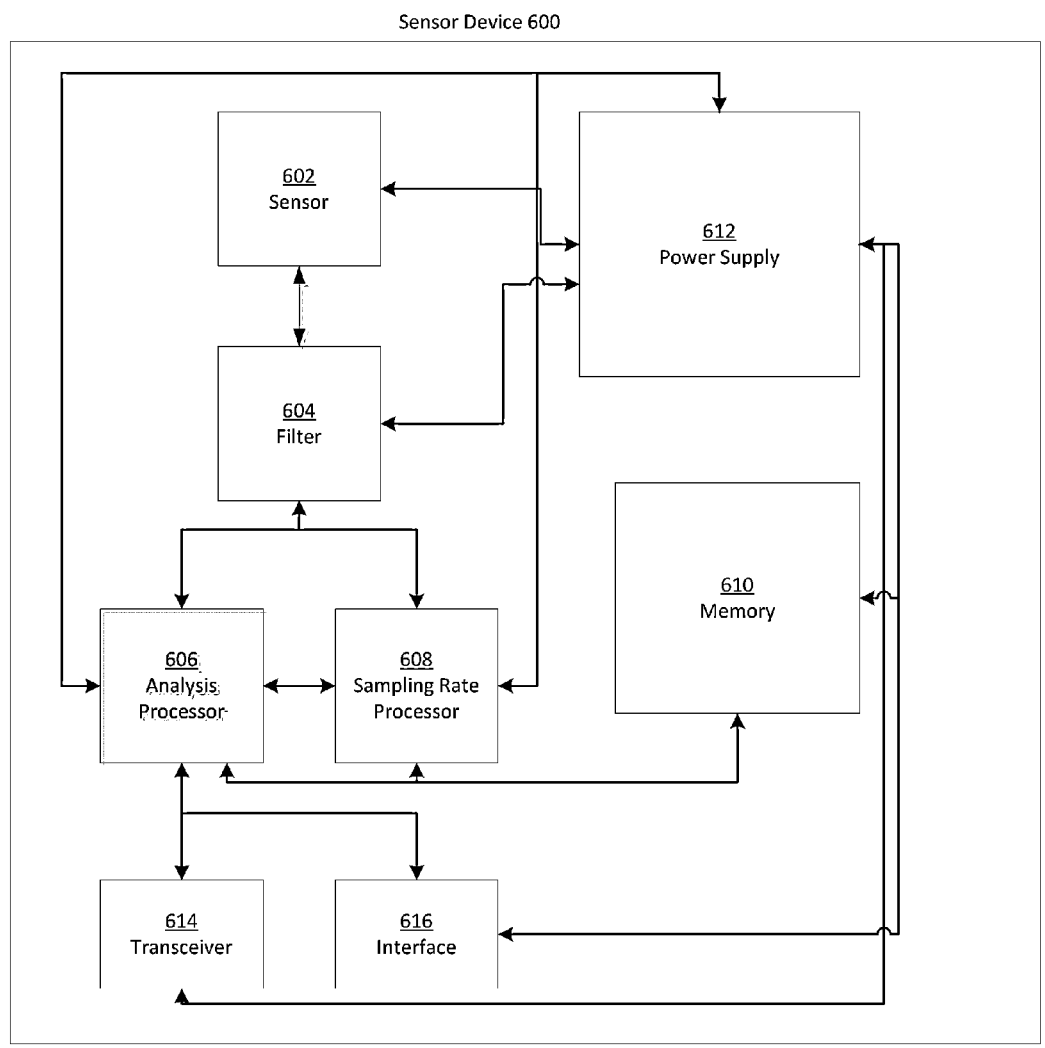
FIG. 6 is a schematic block diagram of an exemplary sensor device 600 that may be utilized in the dynamic adjustment of sampling rates.

FIG. 6 depicts a schematic block diagram of an example sensor device 600 is configured to dynamically adjust one or more sampling rates in accordance with certain embodiments. As shown, sensor device 600 may be embodied with (and/or in operative communication with) elements configurable to dynamically adjust sampling rates of the sensor device. In accordance with one embodiment, by adjusting one or more sampling rates, sensor device 600 can bring about a reduction in power consumption by one or more integral components. Illustrative sensor device 600 is shown as having a sensor 602, a filter 604, an analysis processor 606, a sampling rate processor 608, a memory 610, a power supply 612, a transceiver 614, and an interface 616. However, one of ordinary skill in the art will realize that FIG. 6 is merely one illustrative example of sensor device 600, and that sensor device 600 may be implemented using a plurality of alternative configurations, without departing from the scope of the processes and systems described herein. Additionally, sensor device 600 may include one or more components of computing system 200 of FIG. 2, wherein sensor device 600 may be considered to be part of a larger computer device, or may itself be a stand-alone computer device. Accordingly, in one implementation, sensor device 600 may be configured to perform, partially or wholly, the processes of controller 404 from FIG. 4. In such an implementation, sensor device 600 may be configured to, among other things, bring about a reduction in power consumption by a wrist-worn device 400 used for capturing data on an activity being performed by a user, and thereby, in one embodiment, prolonging a battery life of the device 400.

In one implementation, power supply 612 may comprise a battery. Alternatively, power supply 612 may be a single cell deriving power from stored chemical energy (a group of multiple such cells commonly referred to as a battery), or may be implemented using one or more of a combination of other technologies, including solar cells, capacitors, which may be configured to store electrical energy harvested from the motion of device 400 in which sensor device 600 may be positioned, a supply of electrical energy by "wireless" induction, or a wired supply of electrical energy from a power mains outlet, such as a universal serial bus (USB 1.0/1.1/2.0/3.0 and the like) outlet, and the like. It will be readily understood to one of skill that the systems and methods described herein may be suited to reducing power consumption from these, and other power supply 612 embodiments, without departing from the scope of the description.

In one implementation, sensor 602 of sensor device 600 may include one or more accelerometers, gyroscopes, location-determining devices (GPS), light sensors, temperature sensors, heart rate monitors, image-capturing sensors, microphones, moisture sensor, force sensor, compass, angular rate sensor, and/or combinations thereof among others. As one example embodiment comprising an accelerometer, sensor 602 may be a three-axis (x-, y-, and z-axis) accelerometer implemented as a single integrated circuit, or "chip", wherein acceleration in one or more of the three axes is detected as a change in capacitance across a silicon structure of a microelectromechanical system (MEMS) device. Accordingly, a three-axis accelerometer may be used to resolve an acceleration in any direction in three-dimensional space. In one particular embodiment, sensor 602 may include a STMicroelectronics LIS3DH 3-axis accelerometer package, and outputting a digital signal corresponding to the magnitude of acceleration in one or more of the three axes to which the accelerometer is aligned. One of ordinary skill will understand that sensor 602 may output a digital, or pulse-wave modulated signal, corresponding to a magnitude of acceleration. The digital output of sensor 602, such as one incorporating an accelerometer for example, may be interpreted as a time-varying frequency signal, wherein a frequency of the output signal corresponds to a magnitude of acceleration in one or more of the three axes to which the sensor 602 is sensitive. In alternative implementations, sensor 602 may output an analog signal as a time-varying voltage corresponding to the magnitude of acceleration in one or more of the three axes to which the sensor 602 is sensitive. Furthermore, it will be understood that sensor 602 may be a single-axis, or two-axis accelerometer, without departing from the scope of the embodiments described herein. In yet other implementations, sensor 602 may represent one or more sensors that output an analog or digital signal corresponding to the physical phenomena to which the sensor 602 is responsive.

Optionally, sensor device 600 may include a filter 604, wherein filter 604 may be configured to selectively remove certain frequencies of an output signal from sensor 602. In one implementation, filter 604 is an analog filter with filter characteristics of low-pass, high-pass, or band-pass, or filter 604 is a digital filter, and/or combinations thereof. The output of sensor 602 is transmitted to filter 604, wherein, in one implementation, the output of an analog sensor 602 will be in the form of a continuous, time-varying voltage signal with changing frequency and amplitude. In one implementation, the amplitude of the voltage signal corresponds to a magnitude of acceleration, and the frequency of the output signal corresponds to the number of changes in acceleration per unit time. Filter 604 may be configured to remove those signals corresponding to frequencies outside of a range of interest for activity characterization/recognition and logging by an activity monitoring device, such as device 400. For example, filter 604 may be used to selectively remove high frequency signals over, for example, 100 Hz, which represent motion of sensor 602 at a frequency beyond human capability. In another implementation, filter 604 may be used to remove low-frequency signals from the output of sensor 602 such that signals with a frequency that is lower than any signal characteristics associated with a user activity are not processed further by sensor device 600.

Filter 604 may be referred to as a "pre-filter", wherein filter 604 may remove one or more frequencies from a signal output of sensor 602 such that analysis processor 606 does not consume electrical energy processing data, such as for example, one or more frequencies not representative of one or more activities being performed by a user. In this way, pre-filter 604 may reduce overall power consumption by sensor device 600 or a system of which sensor device 600 is part of.

In one implementation, the output of filter 604 is transmitted to both analysis processor 606 and sampling rate processor 608. When sensor device 600 is powered-on in a first state and electrical energy is supplied from power supply 612, both analysis processor 606 and sampling rate processor 608 may receive a continuous-time output signal from sensor 602, wherein the output signal may be filtered by filter 604 before being received by analysis processor 606 and sampling rate processor 608. In another implementation, when sensor device 600 is powered-on in a second state, analysis processor 606 and sampling rate processor 608 receive an intermittent signal from sensor 602. Those skilled in the art will also appreciate that one or more processors (e.g., processor 606 and/or 608) may analyze data obtained from a sensor other than sensor 602.

Figure 2:
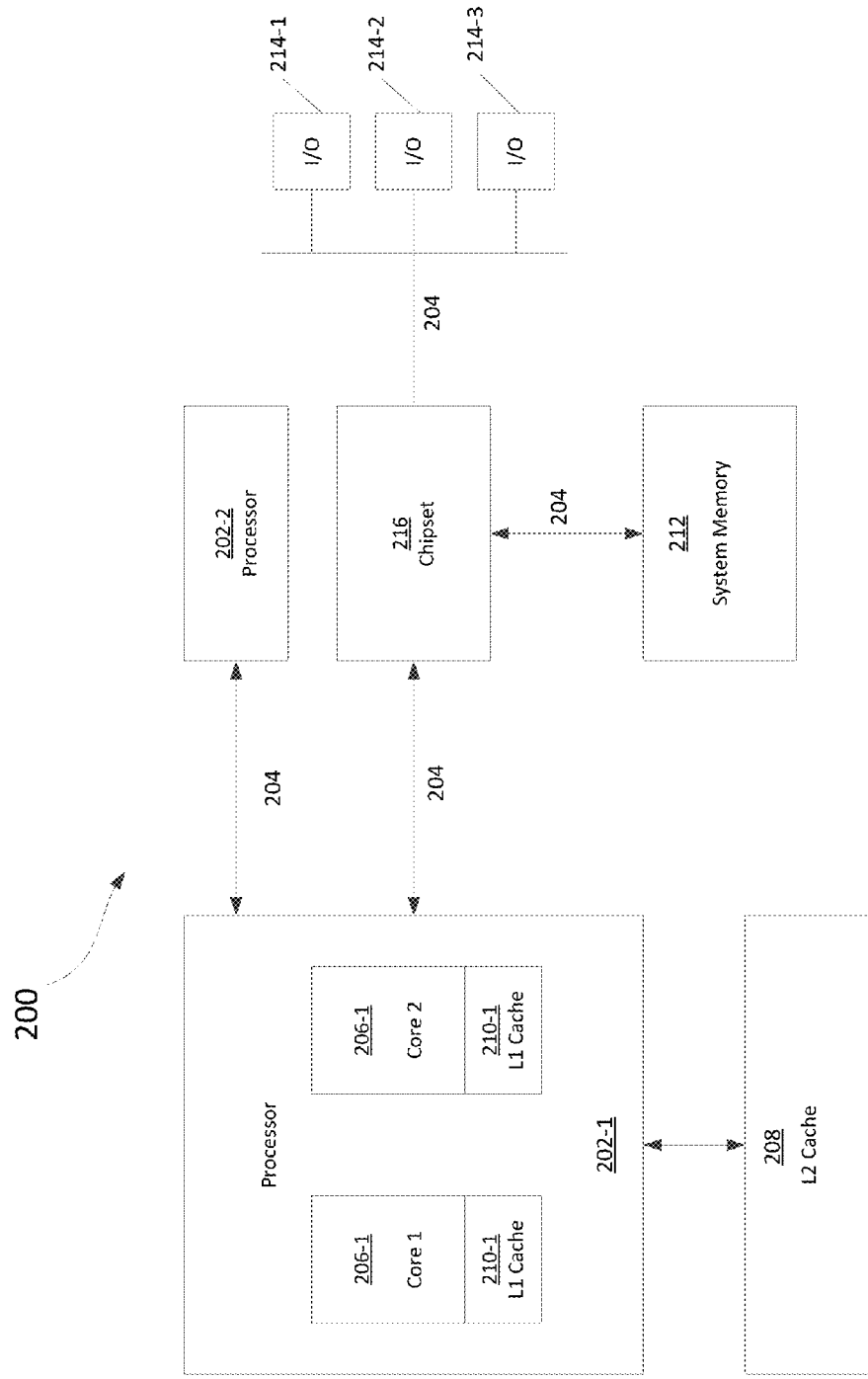
FIG. 2 illustrates an example computer device that may be part of or in communication with the system of FIG. 1.

Sampling rate processor 608 may, in one implementation, have a structure similar to processor 202 from FIG. 2, such that sampling rate processor 608 may be implemented as part of a shared integrated-circuit, or microprocessor device. In another implementation, sampling rate processor 608 may be configured as an application-specific integrated circuit (ASIC), which may be shared with other processes, or dedicated to sampling rate processor 608 alone. Further, it will be readily apparent to those of skill that sampling rate processor 608 may be implemented using a variety of other configurations, such as using discrete analog and/or digital electronic components, and may be configured to execute the same processes as described herein, without departing from the spirit of the implementation depicted in FIG. 6. Similarly, analysis processor 606 may be configured as an ASIC, or as a general-purpose processor 202 from FIG. 2, such that both analysis processor 606 and sampling rate processor 608 may be implemented using physically-separate hardware, or sharing part or all of their hardware.

Memory 610, which may be similar to system memory 212 from FIG. 2, may be used to store computer-executable instructions for carrying out one or more processes executed by analysis processor 606 and/or sampling rate processor 608. Memory 610 may include, but is not limited to, random access memory (RAM), read only memory (ROM), and include one or more of solid-state memory, optical or magnetic storage, and/or any other medium that can be used to store electronic information. Memory 610 is depicted as a single and separate block in FIG. 6, but it will be understood that memory 610 may represent one or more memory types which may be the same, or differ from one another. Additionally, memory 610 may be omitted from sensor device 600 such that the executed instructions are stored on the same integrated circuit as one or more of analysis processor 606 and sampling rate processor 608.

Sampling rate processor 608 may be configured to receive sensor data from sensor 602. In one implementation, upon receipt of the sensor data, sampling rate processor 608 executes one or more processes to compare the sensor data to one or more sampling rate metrics. The sampling rate metrics may include, for example, an amplitude, magnitude, intensity, or a frequency of the data, and/or a change in amplitude or frequency, or combinations of any of the foregoing or other metrics.

The sensor data received from sensor 602 may represent one or more of the three axes for which an accelerometer that is part of sensor 602 is capturing data. Accordingly, sampling rate processor 608 may process the data from one or more of the three axes separately and/or may execute a process to average the data associated with two or more of the axes, which results in an average amplitude and/or frequency. In one implementation, sampling rate processor 608 compares the amplitude of the acceleration signal to one or more threshold sampling rate metrics. By executing a comparison process, the sampling rate processor 608 may access a lookup table stored, in one embodiment, in sampling rate processor 608, or alternatively, in memory 610 or any other non-transitory computer-readable medium. The lookup table may store one or more sampling rates in combination with one or more respective acceleration amplitude threshold values. Generally, successively higher sampling rate values may be stored with successively higher acceleration amplitude values, wherein it is assumed that, in one implementation, when sensor device 600 is implemented in, for example, a wrist worn device 400, more vigorous user activity results in higher acceleration amplitude data values, and benefits from higher sampling rates during analysis by an analysis processor 606.

In one implementation, sampling rate processor 608 executes a comparison process by iterating through the entries in the lookup table in ascending order of stored amplitude threshold values. When the iterating comparison process arrives at an entry in the lookup table with an amplitude threshold value that is greater than the received amplitude value from the sensor 602, it selects the previous, lower, amplitude threshold value, and returns the sampling rate associated with that selected threshold value. However, one of ordinary skill in the art will readily understand that any conventional means of polling/searching through a lookup table may be employed by the sampling rate processor 608 to select a sampling rate that is paired with an amplitude threshold value corresponding to a received amplitude value.

In an alternative implementation in which sensor 602 comprises an accelerometer, sampling rate processor 608 may compare a received acceleration data frequency to one or more acceleration frequency thresholds. In a similar manner to the process described above, the sampling rate processor may store one or more acceleration frequency thresholds in combination with one or more respective sampling rates on a non-transitory computer-readable medium, such as for example, in a lookup table. The sampling rate processor 608, may execute an iterative process through the lookup table until the comparison process arrives at a lookup table entry with an acceleration frequency threshold value that is greater than the received frequency value. In response, the comparison process may select the sampling rate associated with the frequency threshold value that is closest, and below, the frequency value arrived at during iteration. Similar to the stored amplitude threshold value and sampling rate pairs, it may be assumed that higher frequency data received by the sampling rate processor 608 from sensor 602 corresponds to more vigorous activity of a user, and may be sampled at higher sampling rates.

In a further alternative implementation, sampling rate processor 608 executes one or more processes to iteratively search a lookup table for a one or more amplitude or frequency corresponding to one or more stored sampling rates. The sampling rate processor 608 may return a sampling rate corresponding to an amplitude or frequency threshold value that is within a range of a received amplitude or frequency of acceleration from sensor 602.

In one implementation, the frequency threshold values stored in a lookup table may correspond to sampling rates in accordance with the Nyquist sampling theorem (or Nyquist-Shannon sampling theorem), which states that in order to be able to accurately reproduce a signal, it should be sampled at a frequency of at least double the highest frequency present in the signal. For example, for acceleration data received from sensor 602 that includes a range of frequencies, ranging from 25 Hz to 100 Hz, the Nyquist sampling theorem states that in order to accurately reproduce the received acceleration data, it should be sampled at a sampling rate of at least 200 Hz. However, in other implementations, the sampling rates corresponding to stored acceleration frequency thresholds in a lookup table do not consider the Nyquist sampling theorem.

In yet another implementation, sampling rate processor 608 may be configured to compare a change in amplitude or a change in frequency of a data sample from sensor 602. Accordingly, sampling rate processor 608 may temporarily store one or more amplitude values from the received acceleration data in memory 610, and compute the change in amplitude between successively-stored temporary values, or between a pair or non-successively-stored temporary values. A lookup table may store amplitude-change threshold values in combination with respective sampling rates. In one case, the sampling rate processor 608 returns the sampling rate corresponding to a stored amplitude-change threshold value that is closest to, and below, a received acceleration amplitude value from sensor 602. In another case, sampling rate processor 608 returns the sampling rate corresponding to a stored amplitude-change threshold value that is within a range of a received acceleration amplitude value from sensor 602. Similarly, the sampling rate processor 608 may compute a change in frequency for one or more temporarily-stored accelerometer data points, and compare one or more changes in frequency to stored frequency-change threshold values in a lookup table. An iterative search by sampling rate processor 608 through the lookup table may return a sampling rate corresponding to a frequency-change threshold that is, closest to and below, or equal to, or is within a certain range of, a stored frequency-change threshold value.

Furthermore, sampling rate processor 608 may be configured to selectively compare one or more of an amplitude, frequency, amplitude change, or frequency change, among others, from an acceleration data sample using a single lookup table with thresholds, and corresponding sampling rates, stored for one or more of amplitude, frequency, amplitude change, and frequency change.

In view of the foregoing, it will be readily apparent to one of ordinary skill in the art that the systems and processes described herein, and in one implementation, executed by sampling rate processor 608, can alternatively be implemented using sensor data from sensors other than sensor 602. In one alternative implementation, threshold values of light (electromagnetic radiation) intensity or light frequency from a light sensor 602 may be compared to a received light intensity value or light frequency value, or changes in intensity or frequency. Using a similar process to that described in relation to sensor 602, sampling rate processor 608 may query a lookup table for sampling rates corresponding to received light values. Furthermore, and as previously described, sensor device 600 may be implemented with one or more of a variety of sensor types in addition to an accelerometer or light sensor. Accordingly, the processes executed by sampling rate processor 608 may evaluate output values from the respective different sensor types in a similar manner to that described in relation to both the accelerometer and the light sensor.

It is assumed that in certain embodiments, analysis processor 606 may consume a significant portion of the total energy used by sensor device 600, when sampling and analyzing sensor data at a high, or upper sampling rate. For example, analysis processor 606 may sample sensor data from sensor 602 at an upper sampling rate of 50 Hz, and consume 95% of the total electrical energy of sensor device 600. It is further assumed that using a sampling rate that is below a high, or upper sampling rate associated with analysis processor 606 can lead to significant reductions in power consumption. For example, if the sampling rate of the analysis processor 606 is reduced to 24 Hz, the power consumption of sensor device 600 is reduced by 50%. Where power supply 612 is implemented as a battery, this reduction in power consumption can lead to significant increases in battery life between recharges. For example, where the sampling rate of analysis processor 606 is reduced from 50 Hz to 24 Hz, the battery life is doubled. Advantageously, and for a sensor device 600 positioned in a wrist-worn device 400, this may allow a user to wear device 400 for longer periods of time without needing to remove device 400 for recharging.

In one implementation, sampling rate processor 608 receives data from sensor 602 and selects a sampling rate before analysis processor 606 processes said same accelerometer data. The sampling rates selected by sampling rate processor 608 are selected such that they reduce the power consumption of analysis processor 606 while maintaining a sampling rate high enough that the processes executed by analysis processor 606 receive information representative of the output from the sensor 602. As such, the sampling rate is maintained at a rate that may be used to accurately interpret activity metrics from the received sensor data. In this regard, device 600 may have a default sampling rate that is less than the highest achievable sampling rate. In one embodiment, the sampling rate processor 608 executes one or more processes on accelerometer data, selects a sampling rate, and transmits this sampling rate to analysis processor 606. In one implementation, the transmitted sampling rate may range from 0 Hz to 50 Hz, wherein 50 Hz corresponds to an exemplary high, or upper sampling rate for analysis processor 606. In another embodiment, sampling rate processor 606 may transmit a sampling rate ranging from 0 Hz to 100 Hz or 0 Hz to 500 Hz and any other range.

In another implementation, if sampling rate processor 608 determines that a sensed value, such as for example, an acceleration amplitude or frequency value, is not above a stored amplitude or frequency threshold value, it may execute a process to instruct analysis processor 606 not to analyze the acceleration data. This may be the case when, for example, the sensor device 600 is moved briefly, but the movement does not correspond to an activity (or specific type of activity) being performed by a user. This instruction not to analyze the received sensor data may be explicit, with a transmission of a sampling rate of 0 Hz from sampling rate processor 608 to analysis processor 606, or an equivalent instruction not to sample data from sensor 602. Alternatively, the instruction may be implicit, such that sampling rate processor 608 does not transmit instructions to analysis processor 606 if no analysis is to be performed. In this way, analysis processor 606 may remain in a "sleep" state until data of interest (e.g., a threshold level of movement along one or more axis for a first time period) is received. Analysis processor 606 may subsequently be "woken" from this sleep state when sampling rate processor 608 transmits a signal to the analysis processor 606. This wake signal may be a sampling rate frequency, or may be transmitted as a separate message, to a same, or a different input to that receiving a sampling rate. While in the sleep state, analysis processor 606 may consume no energy, or may consume an amount of energy to keep a process active to listen for a wake signal from the sampling rate processor 608.

Analysis processor 606 may be configured to execute processes to recognize one or more activities being carried out by a user, and to classify the one or more activities into one or more activity categories. In one implementation, activity recognition may include quantifying steps taken by the user based upon motion data, such as by detecting arm swings peaks and bounce peaks in the motion data. The quantification may be done based entirely upon data collected from a single device worn on the user's arm, such as for example, proximate to the wrist. In one embodiment, motion data is obtained from an accelerometer. Accelerometer magnitude vectors may be obtained for a time frame and values, such as an average value from magnitude vectors for the time frame may be calculated. The average value (or any other value) may be utilized to determine whether magnitude vectors for the time frame meet an acceleration threshold to qualify for use in calculating step counts for the respective time frame. Acceleration data meeting a threshold may be placed in an analysis buffer. A search range of acceleration frequencies related to an expected activity may be established. Frequencies of the acceleration data within the search range may be analyzed in certain implementations to identify one or more peaks, such as a bounce peak and an arm swing peak. In one embodiment, a first frequency peak may be identified as an arm swing peak if it is within an estimated arm swing range and further meets an arm swing peak threshold. Similarly, a second frequency peak may be determined to be a bounce peak if it is within an estimated bounce range and further meets a bounce peak threshold.

Furthermore, systems and methods may determine whether to utilize the arm swing data, bounce data, and/or other data or portions of data to quantify steps or other motions. The number of peaks, such as arm swing peaks and/or bounce peaks may be used to determine which data to utilize. In one embodiment, systems and methods may use the number of peaks (and types of peaks) to choose a step frequency and step magnitude for quantifying steps. In still further embodiments, at least a portion of the motion data may be classified into an activity category based upon the quantification of steps.

In one embodiment, the sensor signals (such as accelerometer frequencies) and the calculations based upon sensor signals (e.g., a quantity of steps) may be utilized in the classification of an activity category, such as either walking or running, for example. In certain embodiments, if data cannot be categorized as being within a first category (e.g., walking) or group of categories (e.g., walking and running), a first method may analyze collected data. For example, in one embodiment, if detected parameters cannot be classified, then a Euclidean norm equation may be utilized for further analysis. In one embodiment, an average magnitude vector norm (square root of the sum of the squares) of obtained values may be utilized. In yet another embodiment, a different method may analyze at least a portion of the data following classification within a first category or groups of categories. In one embodiment, a step algorithm, may be utilized. Classified and unclassified data may be utilized to calculate an energy expenditure value in certain embodiments.

Exemplary systems and methods that may be implemented to recognize one or more activities are described in U.S. patent application Ser. No. 13/744,103, now U.S. Pat. No. 9,529,966, filed Jan. 17, 2013, the entire content of which is hereby incorporated by reference herein in its entirety for any and all non-limited purposes. In certain embodiments, activity processor 606 may be utilized in executing one or more of the processes described in the herein including those described in the '103 application.

The processes used to classify the activity of a user may compare the data received from sensor 602 to a stored data sample that is characteristic of a particular activity, wherein one or more characteristic data samples may be stored in memory 610.

In one implementation, the activity recognition process and data logging may be executed by analysis processor 606 independently of an initial selection of a sampling rate by sampling rate processor 608 using data received from sensor 602 by the sampling rate processor 608. In this implementation, the activity recognition process may be executed using an initial sampling rate that lies in the middle of a sampling rate range available to the analysis processor 606. In another implementation, the sampling rate processor 608 executes processes to select a sampling rate, and communicates a selected sampling rate with which the analysis processor 606 initializes activity recognition.

The activity recognition processes carried out by analysis processor 606 may result in one or more of a number of outcomes, including; the activity being performed by a user is recognized within a certain confidence interval, or the activity is not recognized. In one implementation, if an activity cannot be recognized by analysis processor 606 after analysis processor 606 processes data sampled at a first sampling rate, the analysis processor 606 sends instructions to sampling rate processor 608 to incrementally increase the sampling rate. In response, sampling rate processor 608 increments the sampling rate, wherein it is assumed that increasing the sampling rate may increase the likelihood of a positive activity recognition outcome. This activity recognition process may be iterative, such that if an activity is not recognized following an increment in sampling rate, the analysis processor 606 instructs sampling rate processor 608 to increment the sampling rate again, and so on, until an upper sampling rate for the analysis processor 606 is reached. In this way, the sampling rate processor 608 attempts to find a low sampling rate to reduce power consumption. However, sampling rate processor 608 attempts to find the low sampling rate, otherwise referred to as a sampling resolution, still high enough to capture data representative of an activity being performed by a user, and such that an activity recognition process will be successful using data captured as the low sampling rate.

In another implementation, if the analysis processor 606 is successful at recognizing an activity being carried out by a user, the analysis processor 606 may instruct the sampling rate processor 608 to decrement the sampling rate. This process of decreasing the sampling rate may continue in an iterative manner until the analysis processor 606 can no longer recognize the incoming accelerometer data.

In another embodiment, the sampling rate processor 608, upon successful or unsuccessful completion of an activity recognition process by analysis processor 606, may execute instructions requesting data from one or more additional sensors 602, wherein the additional sensors may be used to better characterize an activity being performed by a user. Those additional sensors may include one or more of accelerometers, gyroscopes, location-determining devices (GPS), light sensors, temperature sensors, heart rate monitors, image-capturing sensors, microphones, moisture sensor, force sensor, compass, angular rate sensor, or combinations thereof. In yet another embodiment, sampling rate processor 608, upon successful or unsuccessful completion of an activity recognition process, may execute instructions requesting receipt of sensor data from one or more sensors instead of a currently-active sensor 602. In certain embodiments, a first sensor may be adjusted to a first sampling rate and a second sensor may be adjusted to a second sampling rate based upon the sampling rate of the first sensor and/or determination of activity.

Upon successful recognition of an activity being carried out by a user, analysis processor 606 may log samples of the activity data, or execute other processes on the sampled data to extract performance metrics from the data. These logged samples, or extracted performance metrics, may be stored in memory 610.

In yet another implementation, sampling rate processor 608 may execute one or more processes to instruct analysis processor 606 to sample data from sensor 602 at a sampling rate corresponding to a low stored-energy level in power supply 612. This low-battery sampling rate is intended to reduce power consumption by the analysis processor 606 while maintaining a sampling rate that is high enough to capture data representative of an activity being performed by a user.

Sensor device 600 may optionally have a transceiver 614, for communicating stored performance metrics, samples of activity data, and the like, to a computer device, as described in relation to sensor 120 from FIG. 1. Additionally, sensor device 600 may also be configured to have an interface 616, facilitating a physical connection to another device, as described in relation to I/O device 214 from FIG. 2.

Figure 7:
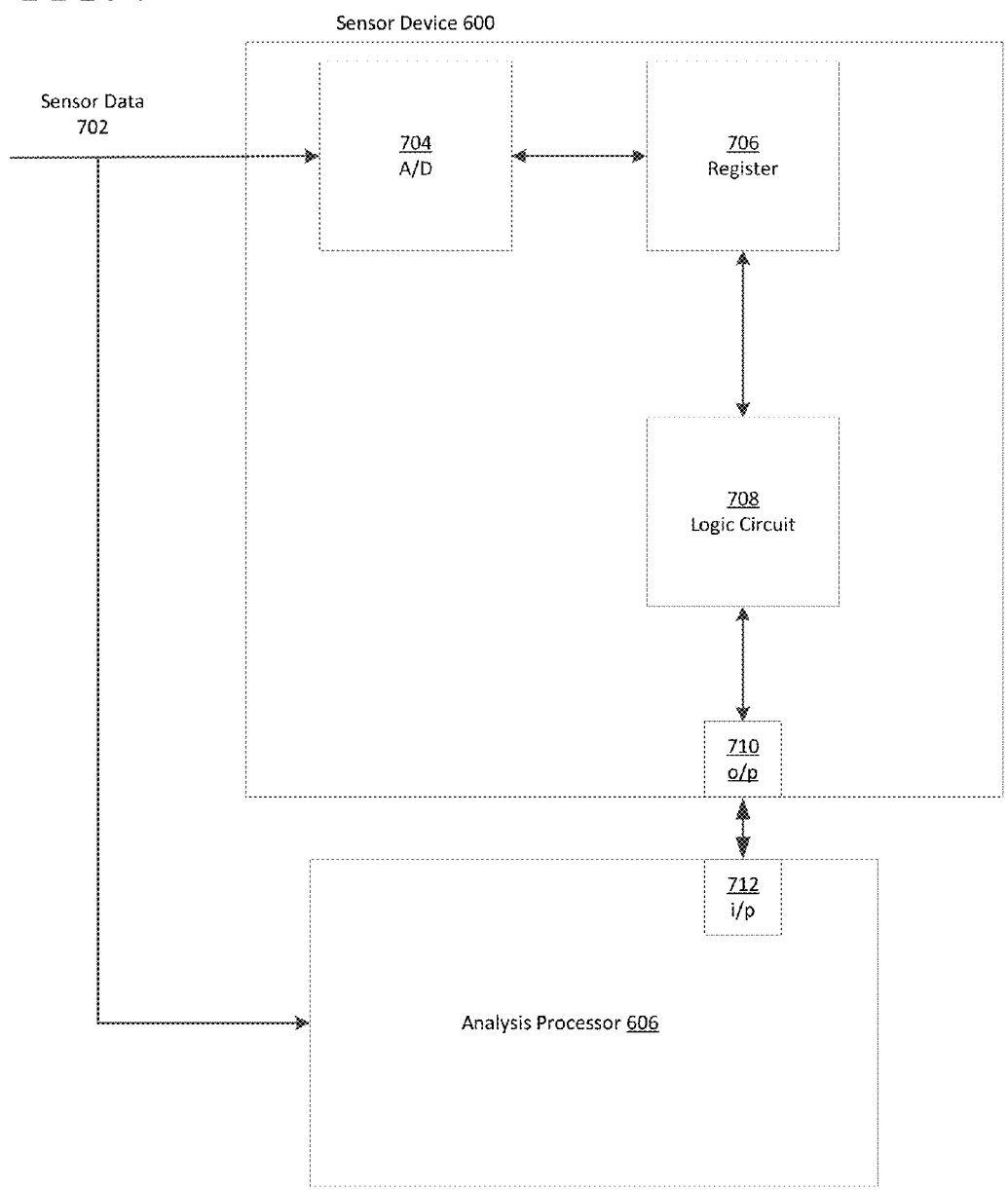
FIG. 7 is a schematic block diagram depicting one implementation of a sampling rate processor, such as the sampling rate processor shown in FIG. 6.

FIG. 7 is a schematic block diagram depicting a more detailed implementation of sampling rate processor 608 from FIG. 6. In particular, FIG. 7 includes a sampling rate processor 608, a sensor data input 702, an analog-to-digital convertor 704, a register 706, a logic circuit 708, an output 710, an input 712, and analysis processor 606.

In one embodiment, sampling rate processor 608 is implemented with an analog-to-digital convertor 704. Analog-to-digital convertor 704 may be employed to convert an analog signal, such as analog sensor data 702 received from sensor 602, into a digital output signal. The digital output from analog-to-digital convertor 704 is transmitted to memory register 706 such that sampling rate processor 608 stores a number of samples of sensor data 702 in digital form. Register 706 may be implemented using a variety of embodiments well known in the art. Logic circuit 708 may be a special-purpose digital circuit comprising a plurality of digital logic gates configured to carry out the sample rate selection processes described in relation to FIG. 6. Alternatively, logic circuit 708 may be a general-purpose array of transistors similar to that of processor 202 from FIG. 2.

Logic circuit 708 may output, among others, a sampling rate at output 710, wherein output 710 is transmitted to input 712 of analysis processor 606. Input 712 may be physical or logical input to analysis processor 606. In one implementation, input 712 is a specific pin of an ASIC, configured to receive a signal corresponding to an instruction for analysis processor 606 to sample sensor data 702 at a specific sampling rate.

Figure 8:
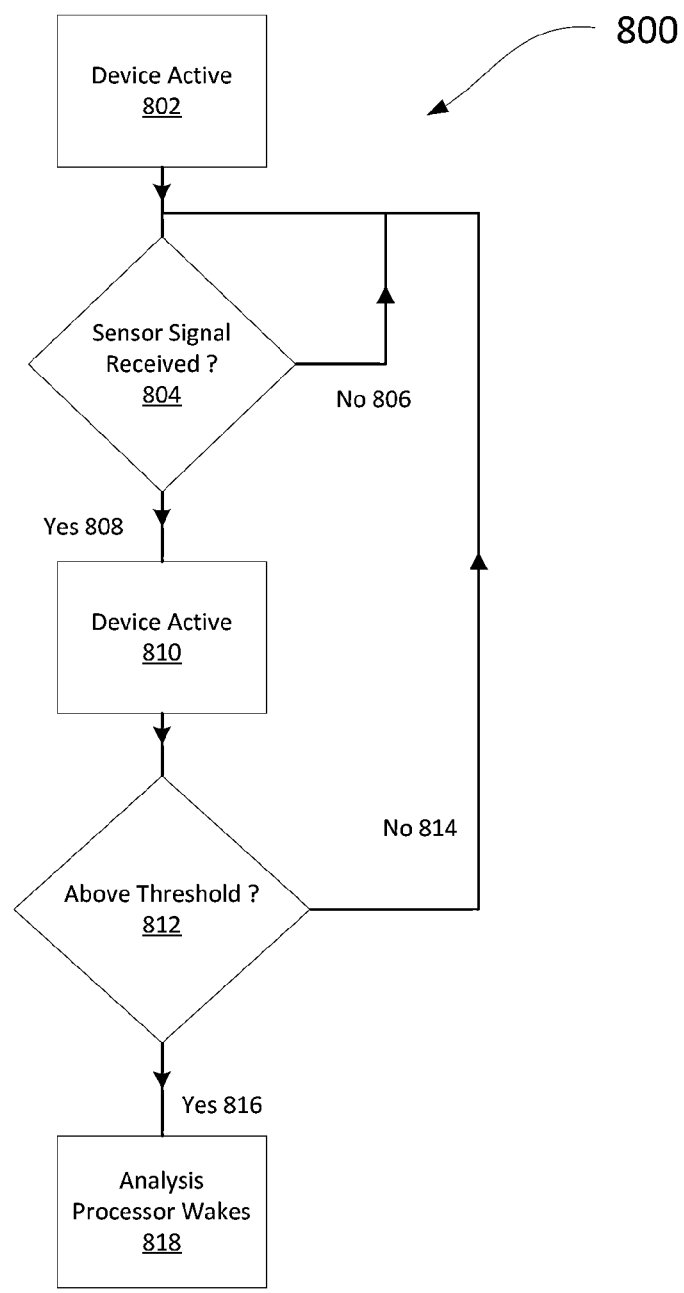
FIG. 8 is a flowchart diagram of an analysis activation process in accordance with one embodiment.

FIG. 8 is a flowchart diagram of an analysis activation process 800 in accordance with one embodiment. Process 800 or a portion thereof may be executed by sensor device 600 from FIG. 6. Process 800 may be initiated at block 802, wherein sensor device 600 is powered on and power supply 612 is supplying electrical energy to one or more of components 602-616. While sensor device 600 is powered on, analysis processor 606 may optionally be in a sleep state, wherein while in the sleep state, analysis processor 606 is not sampling data from sensor 602. Consequently, the sleep state facilitates low power consumption by the analysis processor 606 from power supply 612. Analysis processor 606 may execute processes to enter into the sleep state upon initialization of sensor device 600, or optionally, analysis processor 606 may be instructed to enter into the sleep state at any time, including by a process executed from sampling rate processor 608. In one implementation, sampling rate processor 608 will execute processes to instruct analysis processor 606 to sleep upon expiration of a timeout period between receipt of sensor data from sensor 602 that is above a threshold value.

It may be determined whether a sensor signal is received (e.g., see decision 804). Decision 804 may represent a timeout period during which sampling rate processor 608 is awaiting arrival of new sensor data from sensor 602. For example, sampling rate processor may check (e.g. periodically or based upon an input) for new data, and if no data has been received, the timeout period follows path 806, looping back to block 804. If sampling rate processor 608 is in receipt of new data, path 808 may be followed. The received data may optionally be passed through a filter, such as filter 604, at block 810. The filtered and/or unfiltered sensor data may be further processed by sampling rate processor 608. For example, decision 812 may be implemented to perform one or more comparison processes carried out by sampling rate processor 608, described in further detail in relation to FIG. 6. In one embodiment, the one or more comparison processes may compare the sensor data to one or more threshold values. In one embodiment, if a magnitude of the sensor data signal is not above a threshold value, process 800 may return to block 804 along path 814. Alternatively, if a parameter of the sensor data (e.g. the magnitude of the sensor data) is above a threshold value, sampling rate processor 608 may execute a process to wake analysis processor, and to sample the sensor data at a specific sampling rate (see, e.g., block 818 via path 816). In this way, process 800 may be seen in certain embodiments as a method regarding the activation, or waking, of analysis processor 606 from a sleep mode, such that analysis processor 606 consumes a low amount of energy up until sensor data above a threshold value is received.

Figure 9:
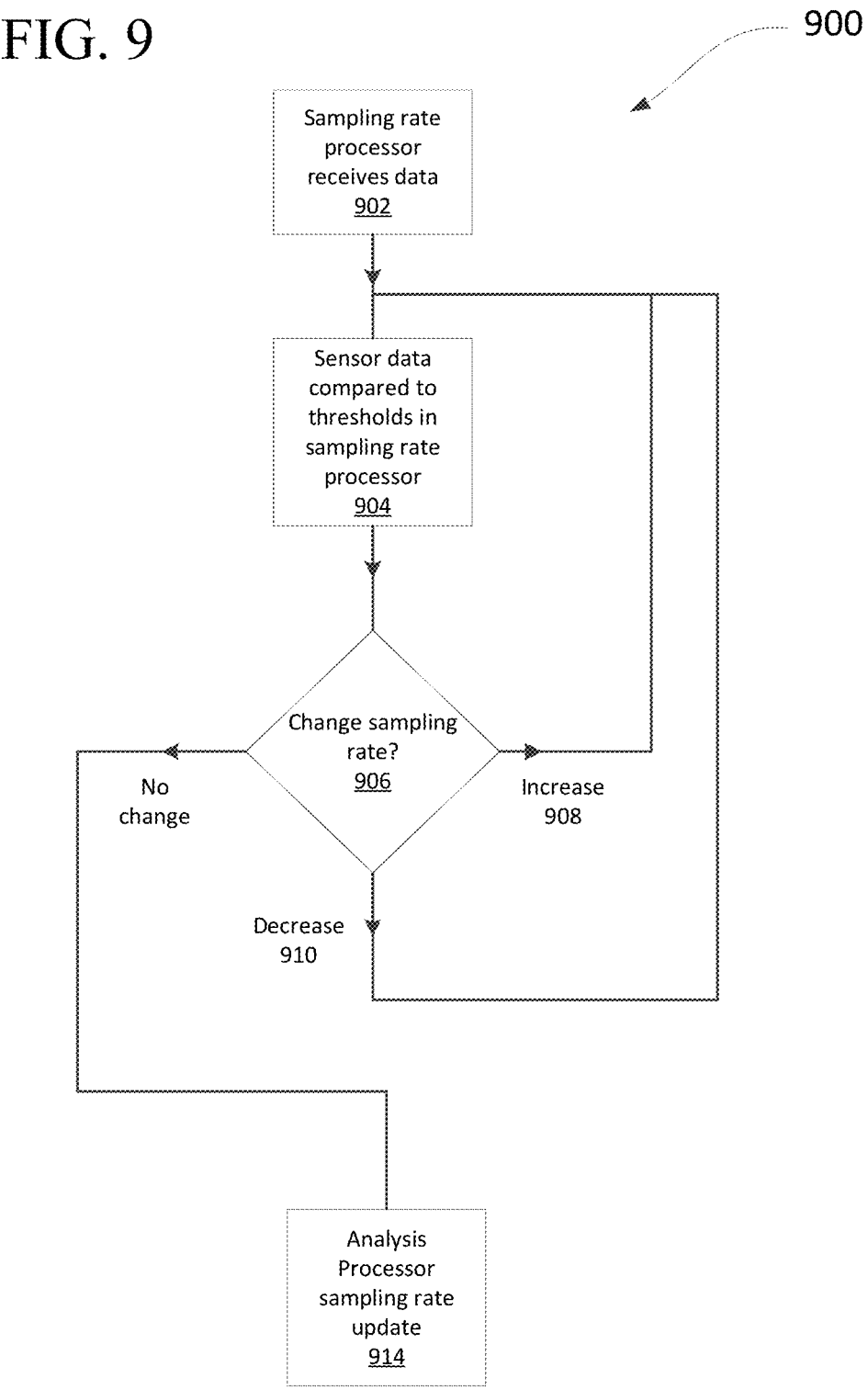
FIG. 9 is a flowchart diagram of a process that may be utilized to adjust one or more sampling rates in accordance with one embodiment.

FIG. 9 is flowchart diagram of a process 900 for adjustment of a sampling rate, such by, for example sampling rate processor 608, in response to receipt of a sensor data signal that has a magnitude above one or more threshold values. Process 900 may be initiated at block 902 as a processor (e.g., sampling rate processor 608) receives sensor data. Simultaneously, another processor (e.g., analysis processor 606) may be sampling the sensor data at a default initialization sampling rate, or predetermined sampling rate. Process 900 proceeds to block 904 wherein sampling rate processor 608 executes one or more comparison processes on the sensor data. These comparison processes may compare an amplitude, a frequency, a change in amplitude, or a change in frequency, among others, of the sensor data signal to one or more threshold values, as described in relation to FIG. 6. Upon calculation, by the sampling rate processor 608, of a threshold value corresponding to, or within a predetermined range of, a value of the sensor data signal, process 900 may proceed to block 906.

Decision 906 may be implemented to determine whether to change or otherwise alter the sampling rate. In this regard, decision 906 may be implemented as a result of sampling rate processor 608 calculating that a magnitude of the sensor data signal corresponds to a threshold value from a plurality of threshold values. The corresponding threshold value has an associated sampling rate value that may be above, below, or equal to a current sampling rate in-use by analysis processor 606. In another implementation, block 904 may compare a magnitude of a sensor data value to a single threshold value. This comparison may result in an instruction from sampling rate processor 608 for analysis processor 606 to adjust its sampling rate to a specific value, or alternatively, when a comparison to a single threshold is employed, to increment or decrement the sampling rate by a predetermined amount. If the current sampling rate in use by analysis processor 906 is less than that specific sampling rate selected, or if the magnitude of the sensor data value is greater than a single threshold value used in the comparison, sampling rate processor may instruct analysis processor 606 to increase its sampling rate, and process 900 may proceed along path 908 to comparison block 904. Conversely, if the current sampling rate used by analysis processor 606 is greater than the calculated sampling rate, or if the magnitude of the sensor signal value is below a single threshold value used for comparison, processor 900 may proceed along path 910, and sampling rate processor may 608 instruct analysis processor 606 to decrease the sampling rate, wherein the decrease in sampling rate may be to a specific sampling rate, or by a predetermined, decrement amount. Paths 908 and 910 represent an iterative loop through blocks 904 and 906 until process 900 arrives at a target sampling rate, wherein the target sampling rate is transmitted to analysis processor 606 for sampling of the sensor data at block 914.

Figure 10:
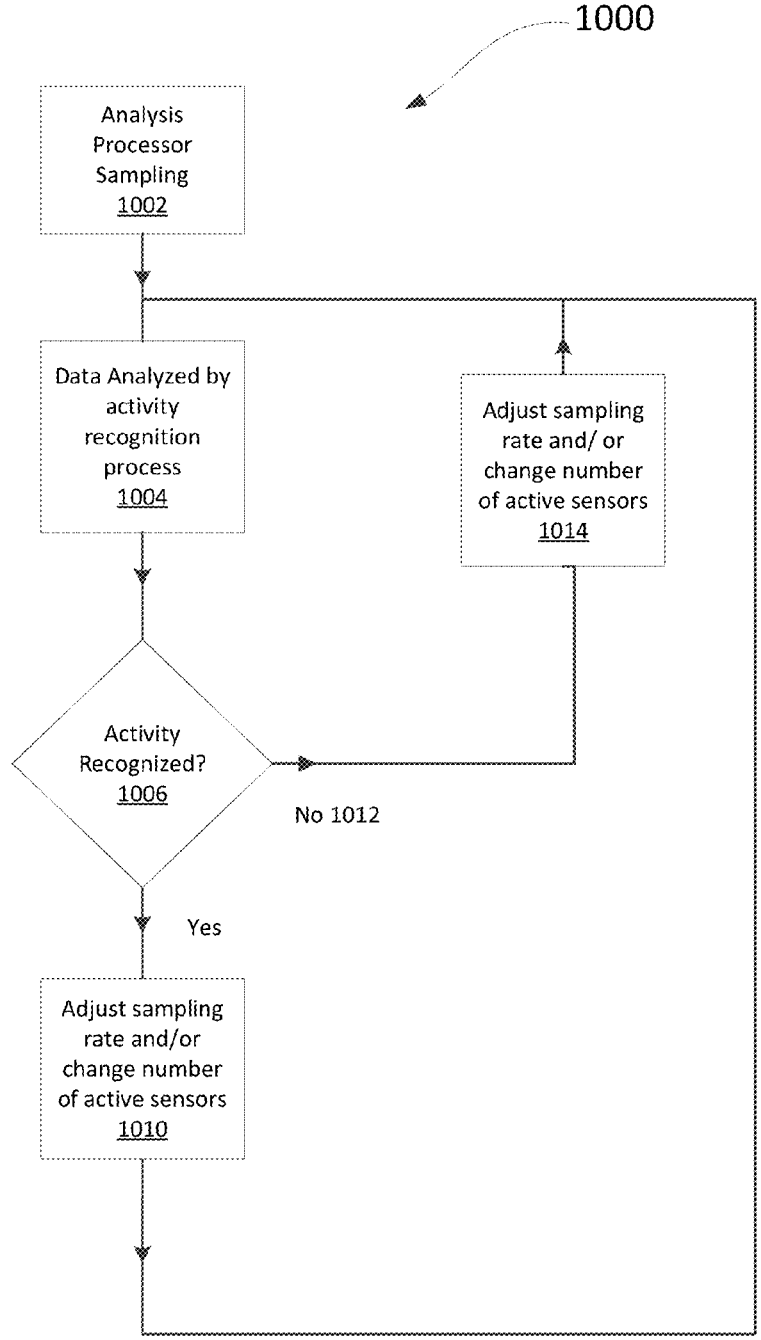
FIG. 10 is a flowchart diagram of a process that may be utilized to adjust sampling rates in response to activity recognition in accordance with one embodiment.

FIG. 10 is a flowchart of a process 1000 that may be utilized in the adjustment of sampling conditions in response to activity recognition. As shown in FIG. 10, block 1002 may be implemented to receive sensor data. For example, analysis processor 606 may be sampling a signal from a sensor (e.g. sensor 602). In further embodiments, sensor data received at 1002 may be filtered and/or processed sensor data. In one embodiment, only data passing a threshold may be received or otherwise considered at block 1002. As one example, process 1000 may have one or more aspects that are similar or identical to decision 812 when determining what data is received or utilized. Sensor data may be analyzed using one or more activity recognition processes such as described above in relation to analysis processor 606 (see, e.g. block 1004). Decision 1006 may be implemented to determine whether one or more activity recognition processes were successful at classifying the sensor data into an activity classification. In response to the activity recognition processes being unsuccessful, path 1012 may be followed to block 1014. Block 1014 may increase the sampling rate at which sensor data from at least one is sampled, and/or may instruct one or more additional or alternative sensors to be used to capture information about the activity being performed. In one embodiment, block 1014 may be performed, at least partially, by analysis processor 606. Those skilled in the art will appreciate that block 1014 is merely an example. Other embodiments may retain the current sampling rate and/or selected sensors. In certain embodiments, the number of sensors utilized and/or the sampling rate may be decreased. For example, if a specific activity (or type of activity) is not detected, the sampling rate may decrease to preserve battery life. In certain embodiments, parameters of the data may indicate whether the sampling rate or number of sensors is altered (either increased or decreased). For example, large amounts of motion from a single axis may be treated differently than lower quantities of motion from multiple axes.

Looking back to decision 1006, if the one or more activity recognition processes are successful in classifying the activity of a user into an activity classification, process 1000 proceeds from decision point 1006 to block 1010, wherein the sampling rate or quantity of sensors utilized may be adjusted in a manner than would be performed if block 1014 was implemented. For example, in one embodiment, sampling rate processor 608 may instruct analysis processor 606 to decrease its sampling rate, or change the number or type of sensors from which information about the activity of the user is being captured. In this way, a decrease in sampling rate, use of alternative sensors more capable of capturing data related to the determined activity, or use of a lower number of sensors, sensor device 600 is configured to consume less power.

In further embodiments, further data is collected at the adjusted sampling rate from the selected sensor(s), which may be compared to one or more threshold values. In one embodiment, one or more processes similar or identical to block 804 may be implemented. Thus, the data may be compared to a threshold value periodically or after a first time interval (e.g., every 1 second or 5 seconds) to determine whether to adjust the sampling rate and/or sensors utilized without regard to whether the activity has changed in the meantime. For example, activity determinations may only be conducted after a duration that is longer than the first time frame (e.g., every 10 seconds). Thus, two or more variables (e.g., threshold levels of sensor data and activity determinations) may be utilized independently to adjust the sampling rate or sensors utilized. Those skilled in the art will appreciate that activity determinations may be performed at a time interval that is less than threshold level determinations. In this regard, a first sensor may be utilized at a first sampling rate if a first threshold level is obtained when a first activity is detected and not at all if a second activity is detected regardless of whether a threshold level of sensor data is obtained. Similarly, a second sensor may be utilized regardless of what activity is sensed and the sampling rate may be influenced by the threshold level of sampling data.

Figure 11:
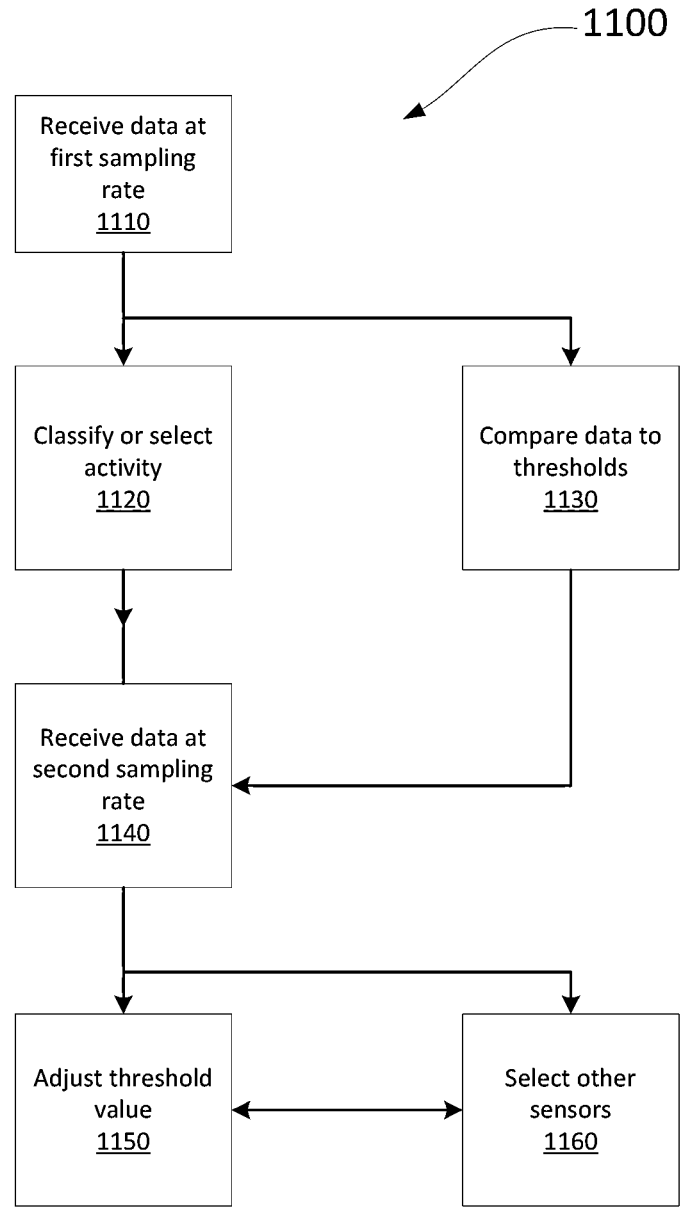
FIG. 11 is a flowchart diagram of a process which may be executed by a sensor device, such as the sensor device of FIG. 6, in accordance with one embodiment.

FIG. 11 is a flowchart diagram of process 1100 which may be executed by, in one embodiment, one or more components of sensor device 600 from FIG. 6, among others. In one implementation, analysis processor 606 from FIG. 6 may receive data at a first sampling rate, as indicated by block 1110. The data received at the first sampling rate may be representative of, among others, an activity being carried out by a user of sensor device 600, wherein the activity being carried out may be a sporting activity. The first sampling rate may be determined by sampling rate processor 608 based on, among others, a default sampling rate communicated from sampling rate processor 608 to analysis processor 606 upon initialization of sensor device 600. In another implementation, the first sampling rate may be a last-used sampling rate, such as for example, by analysis processor 606, as communicated to analysis processor 606 by sampling rate processor 608, wherein the last-used sampling rate may be, in one implementation, the sampling rate at which a processor, such as analysis processor 606, sampled data prior to sensor device 600 being powered-off, or instructed to enter into a sleep mode.

Block 1120 may be implemented to select or classify the received data into an activity category, wherein an activity category is representative of one or more activities being carried out by a user being monitored by sensor device 600, among others. The user may be wearing sensor device 600, yet in other embodiments, a camera and/or other sensors may be utilized to monitor the user's activity without being in physical communication with the user. The selection of a category or classification of the received data into an activity category may be based upon, among others, a selected activity category by a user, a recognized activity category, wherein one or more activity recognition processes may be executed by analysis processor 606. The selected activity category may also be a default activity category, wherein the default activity category may be selected by analysis processor 606 upon initialization of sensor device 600, or a last-known activity category used by analysis processor 606.

In another implementation, as indicated as block 1130, the data received, such as by analysis processor 606, may be compared to one or more threshold values. For example, the received data may have one or more numerical values such that one or more processes may be executed by analysis processor 606, among others, to determine if the one or more numerical values are within a range of a first threshold value, closest to, but above a first threshold value, or equal to a first threshold value, among others. In one embodiment, and in response to determining, such as by analysis processor 606, that one or more of the received numerical values corresponds to one or more first threshold values, the received data may be classified into one or more activity categories, such as by analysis processor 606. Selection or classification of the received data into one or more activity categories may be based on the corresponding first threshold values, wherein the one or more first threshold values further corresponds to one or more activity categories.

In another embodiment, data may be received, such as by analysis processor 606, at a second sampling rate. The second sampling rate may be selected by sampling rate processor 608, such that sensor device 600 may, among others, consume less power, or receive data at a sampling rate that is representative of the activity being carried out by a user. Block 1140 represents one or more processes for receiving data at a second sampling rate. In one implementation, the second sampling rate may be based on at least one or more activity categories into which the data received from the user was classified, such as by analysis processor 606, and as described in relation to block 1120. In another implementation, the second sampling rate is based on at least one or more threshold values corresponding to the received data, wherein the first threshold values are described in relation to block 1130. The second sampling rate may, in one implementation, be higher than the first sampling rate, such that data is sampled more frequently. In yet another implementation, however, the second sampling rate may be lower than the first sampling rate, such that data is sampled less frequently, and there is a corresponding decrease in power consumption by, among others, analysis processor 606.

Block 1150 represents one or more processes corresponding to a selection, such as by sampling rate processor 608, of one or more second threshold values. The one or more second threshold values are selected, by sampling rate processor 608, based on the one or more first threshold values, or a classification of activity data into an activity classification, or combination thereof. In one implementation, the one or more second threshold values are selected in response to the received data having a numerical value above, within a predefined range of, or equal to a first threshold value, and the received data being classified into an activity classification. In this way, when the received data corresponds to one or more first threshold values, in combination with the received data are being classified into one or more activity classifications, one or more new, or second, sampling rates may be selected (such as by sampling rate processor), and re-evaluates the received data. In one exemplary embodiment, the processes corresponding to block 1150 may be executed if, for example, a value of data received is above a threshold corresponding to vigorous activity, and the received data has been classified into, for example, an activity classification corresponding to playing basketball. In response, sampling rate processor 608 may select a second threshold value corresponding to light activity, and sampling rate processor 608 may not adjust the sampling rate of analysis processor 606 until data is received with a value corresponding to this light activity threshold.

Block 1160 corresponds to one or more processes, executed by sampling rate processor 608, wherein sampling rate processor 608 may select one or more sensors to receive activity data from. In one implementation, the one or more sensors selected may be in addition to one or more currently-used sensors from which data is received by analysis processor 606 at block 1110. In another implementation, the one or more selected sensors may replace the one or more currently-used sensors from which data is received at block 1110. The one or more sensors selected at block 1160 may be selected based on, among others, the second sampling rate, or the activity classification into which the received data has been classified, wherein the one or more sensors may be selected for being relatively more efficient and/or effective at receiving data corresponding to the activity classification or the second sampling rate.

For the avoidance of doubt, the present application extends to the subject-matter described in the following numbered paragraphs (referred to as "Para" or "Paras"):

1. A unitary apparatus configured to be worn by a user, comprising:
   a power supply;
   a sensor arranged to capture acceleration data from an appendage of the user;
   a sampling rate processor arranged to receive the captured acceleration data and determine a first sampling rate; and
   an analysis processor arranged to sample the data captured by the sensor at the first sampling rate and analyze the sampled data so as to classify the acceleration data into an activity category being performed by the user;
   wherein the sampling rate processor attempts to choose the first sampling rate with a value below an upper sampling rate in order to reduce power consumption by the analysis processor from the power supply during sampling.

2. The unitary apparatus of Para 1, wherein the sampling rate processor is further configured to:
   compare a value of the acceleration data to a threshold value; and
   determine the first sampling rate as corresponding to the threshold value.

3. The unitary apparatus of Para 2, wherein the sampling rate processor determines the first sampling rate corresponding to the threshold value when the value of the acceleration data is equal to the threshold value.

4. The unitary apparatus of Para 2, wherein the sampling rate processor determines the first sampling rate corresponding to the threshold value when the value of the acceleration data is numerically closer to, and greater than, a second threshold value.

5. The unitary apparatus of Para 2, wherein the sampling rate processor determines the first sampling rate corresponding to the threshold value when the value of the acceleration data is within a range of the threshold value.

6. The unitary apparatus of any of Paras 2 to 5, wherein the value of the acceleration data is an amplitude.

7. The unitary apparatus of any of Paras 2 to 5, wherein the value of the acceleration data is a frequency.

8. The unitary apparatus of any preceding Para, wherein the sampling rate processor determines the first sampling rate as a low-battery sampling rate corresponding to a low level of stored electrical energy in the power supply.

9. The unitary apparatus of any preceding Para, wherein the analysis processor is further configured to store sampled acceleration data corresponding to the classified activity category in a non-transitory computer-readable medium.

10. The unitary apparatus of any preceding Para, wherein the sampling rate processor is further configured to:

determine a second sampling rate corresponding to the activity category into which the acceleration data is classified, and in response to the determined second sampling rate, storing, by the analysis processor, acceleration data sampled at the second sampling rate.

11. The unitary apparatus of Para 10, wherein the second sampling rate corresponds to a low power consumption rate by the analysis processor, while maintaining a sampling resolution to capture data for the classified activity category.

12. The unitary apparatus of any preceding Para, further comprising: a filter, for selectively filtering out a signal from the captured acceleration data.

13. The unitary apparatus of any preceding Para, further comprising a memory register circuit which is arranged to store the captured acceleration data received by the sampling rate processor.

14. The unitary apparatus of any preceding Para, wherein the sampling rate processor is further configured to:
select, in response to the classification of the acceleration data into an activity category, a second sensor from which to capture data about the activity of the user.

15. The unitary apparatus of any preceding Para, wherein the sampling rate processor is further configured to:
select, in response to receipt of the captured acceleration data, a second sensor from which to capture data about the activity of the user.

16. The unitary apparatus of any preceding Para, further comprising: a transceiver, for communicating the sampled data to a portable computer system.

17. The unitary apparatus of any preceding Para, wherein the first sampling rate ranges from 0 Hz to 50 Hz.

18. A computer-implemented method for reducing power consumption by a sensor apparatus, comprising:
capturing, by a sensor located on a device configured to be worn on an appendage of a user, acceleration data for the appendage of the user;
receiving, by a sampling rate processor of the device, the captured acceleration data;
determining, by the sampling rate processor, a first sampling rate for the sensor, by selecting the first sampling rate that is below an upper sampling rate in order to reduce power consumption by an analysis processor during sampling;
sampling, by the analysis processor, data captured by the sensor at the first sampling rate; and
analyzing, by the analysis processor, the sampled data in an attempt to classify the acceleration data into an activity category being performed by the user.

19. The method according to Para 18, further comprising:
comparing, by the sampling rate processor, a value of the acceleration data to a threshold value; and
determining, by the sampling rate processor, the first sampling rate as corresponding to the threshold value.

20. The method according to Para 19, further comprising:
determining, by the sampling rate processor, the first sampling rate corresponding to the threshold value when the value of the acceleration data is equal to the threshold value.

21. The method according to Para 19, further comprising:
determining, by the sampling rate processor, the first sampling rate corresponding to the threshold value when the value of the acceleration data is numerically closer to, and greater than, a second threshold value.

22. The method according to 19, further comprising:
determining, by the sampling rate processor, the first sampling rate corresponding to the threshold value when the value of the acceleration data is within a range of the threshold value.

23. The method according to Para 19, wherein the value of the acceleration data is an amplitude.

24. The method according to Para 19, wherein the value of the acceleration data is a frequency.

25. The method according to any of Paras 18 to 24, further comprising:
determining, by the sampling rate processor, the first sampling rate as a low-battery sampling rate corresponding to a low level of stored electrical energy in the power supply.

26. The method according to any of Paras 18 to 25, further comprising:
storing, by the analysis processor, sampled acceleration data corresponding to the classified activity category in a non-transitory computer-readable medium.

27. The method according to any of Paras 18 to 26, further comprising:
determining, by the sampling rate processor, a second sampling rate corresponding to the activity category into which the acceleration data is classified, and in response to the determined second sampling rate, storing, by the analysis processor, acceleration data sampled at the second sampling rate.

28. The method according to Para 27, wherein the second sampling rate corresponds to a low power consumption rate by the analysis processor, while maintaining a sampling resolution to capture data for the classified activity category.

29. The method according to any of Paras 18 to 28, further comprising: selectively filtering out a signal from the captured acceleration data, by a filter.

30. The method according to any of Paras 18 to 29, further comprising:
receiving, by the sampling rate processor, the captured acceleration data into a memory register circuit.

31. The method according to any of Paras 18 to 30, further comprising:
selecting, by the sampling rate processor, and in response to the classification of the acceleration data into an activity category, a second sensor from which to capture data about the activity of the user.

32. The method according to any of Paras 18 to 30, further comprising:
selecting, by the sampling rate processor, and in response to receipt of the captured acceleration data, a second sensor from which to capture data about the activity of the user.

33. The method according to any of Paras 18 to 32, wherein the first sampling rate ranges from 0 Hz to 50 Hz.

The present application also extends to the subject-matter described in the following numbered paragraphs:

A1. A non-transitory computer-readable medium comprising computer-executable instructions that when executed by a processor is configured to perform at least:
receiving acceleration data representing movement of an appendage of a user at a sampling rate processor located on a device configured to be worn on an appendage of a human, wherein the acceleration data was obtained by an accelerometer located on the device that is operating at a first sampling rate;
classifying the acceleration data into one of a plurality of activity categories representing an activity being performed by the user; and based upon at least the classified activity category, selecting a second sampling rate for operating the accelerometer.

A2. The non-transitory computer-readable medium of Para A1, wherein the medium further comprises computer-executable instructions that when executed further perform at least:
comparing a first value of acceleration data obtained from the accelerometer during operation at the first sampling rate against a plurality of threshold values;
determining that the first value of acceleration data corresponds to a first threshold value within the plurality of threshold values; and
wherein the selection of the second sampling rate is based upon both the correspondence of the first value of acceleration data to the first threshold value and the classified activity category.

A3. The non-transitory computer-readable medium of Para A2, wherein determining the first sampling rate corresponds to the threshold value occurs at a sampling rate processor located on the device and is based upon at least one of: the first value of the acceleration data is equal to the threshold value, the first value of the acceleration data is numerically closer to, and greater than, a second threshold value, the first value of the acceleration data is within a range of the threshold value.

A4. The non-transitory computer-readable medium of any preceding Para, wherein the first value of the acceleration data comprises at least one of: an amplitude or a frequency.

A5. The non-transitory computer-readable medium of any preceding Para, wherein the accelerometer is a first accelerometer and the medium further comprises computer-executable instructions that when executed further perform at least:
selecting a second sensor that is not the first accelerometer to capture motion data from the user based upon at least one of: (a) the correspondence of the first value of acceleration data to the first threshold value and (b) the classified activity category.

A6. The non-transitory computer-readable medium of Para A5, wherein after selecting of the second sensor, the first accelerometer and the second sensor are utilized to capture the user's movement.

A7. The non-transitory computer-readable medium of Para A5, wherein after selecting the second sensor, the first accelerometer is not used to capture the user's movement.

A8. The non-transitory computer-readable medium of any preceding Para, wherein the accelerometer is a first accelerometer and the medium further comprises computer-executable instructions that when executed further perform at least:
comparing a value of acceleration data obtained from the first accelerometer during its operation at the first sampling rate to a plurality of threshold values;
determining that the value of acceleration data corresponds to a first threshold value within the plurality the threshold values; and
based upon the correspondence to the first threshold value and the classified activity category, selecting a second threshold value.

A9. The non-transitory computer-readable medium of any preceding Para, wherein the sampling rate processor determines the first sampling rate as a low-battery sampling rate corresponding to a low level of stored electrical energy in the power supply.

A10. A non-transitory computer-readable medium comprising computer-executable instructions that when executed by a processor is configured to perform at least:
a) receiving, from an accelerometer of a processor, acceleration data;
b) identifying an activity from the received acceleration data;
c) adjusting a sampling rate of the accelerometer based on the activity identified in b).

A11. The non-transitory computer-readable medium of Para A10, wherein the medium further comprises computer-executable instructions that when executed further perform at least:
comparing a first value of acceleration data obtained from the accelerometer during operation against a plurality of threshold values;
determining that the first value of acceleration data corresponds to a first threshold value within the plurality the threshold values; and
wherein the adjustment of the sampling rate is based upon the correspondence of the first value of acceleration data to the first threshold value.

A12. The non-transitory computer-readable medium of Para A10 or A11, wherein the accelerometer is a first accelerometer and the medium further comprises computer-executable instructions that when executed further perform at least:
selecting a second sensor that is not the first accelerometer to capture motion data based upon the correspondence of the first value of acceleration data to the first threshold value.

A13. The non-transitory computer-readable medium of Para A12, wherein after selecting of the second sensor, the first accelerometer and the second sensor are utilized to capture motion data.

A14. The non-transitory computer-readable medium of Para A12, wherein after selecting of the second sensor, the first accelerometer is not used to capture motion data.

A15. The non-transitory computer-readable medium of any of Paras A10 to A14, wherein the accelerometer is a first accelerometer and the medium further comprises computer-executable instructions that when executed further perform at least:
comparing a value of acceleration data obtained from the first accelerometer during its operation at the first sampling rate to a plurality of threshold values;
determining that the value of acceleration data corresponds to a first threshold value within the plurality the threshold values; and
based upon the correspondence to the first threshold value and the classified activity category, selecting a second threshold value.

A16. A unitary apparatus configured to be worn by a user, comprising:
a structure configured to be worn around an appendage of a user, comprising:
a power supply;
a sensor configured to capture acceleration data from the appendage of the user;
an analysis processor;
a sampling rate processor; and
the non-transitory computer-readable medium of any preceding Para.

What is claimed is:

1. A non-transitory computer-readable medium comprising computer-executable instructions that when executed by a processor is configured to perform at least:

receive acceleration data representing movement of an appendage of a user at a sampling rate processor located on a device configured to be worn on an appendage of a human, wherein the acceleration data was obtained by an accelerometer located on the device while the accelerometer is operating at a first sampling rate;

based, at least in part, on the received acceleration data itself, classify the acceleration data into one of a plurality of activity categories representing sporting activity, recognized from a plurality of sporting activities, being performed by the user; and based upon at least the sporting activity, selecting a second sampling rate of hardware of the accelerometer, from a plurality of sampling rates for operating the accelerometer during the activity being performed by the user, wherein the selection of the first sampling rate and the second sampling rate are selected to prolong a battery life of the device, wherein the accelerometer is a first accelerometer and the medium further comprises computer executable instructions that when executed further perform at least:

compare a value of acceleration data obtained from the accelerometer during its operation at the first sampling rate to a plurality of threshold values;

determining that the value of acceleration data corresponds to a first threshold value within the plurality the threshold values; and based upon the correspondence to the first threshold value and a classified activity category, selecting a second threshold value.

2. The non-transitory computer-readable medium of claim 1, wherein the medium further comprises computer-executable instructions that when executed further perform at least:

compare, with a processor located on the device, a first value of acceleration data obtained from the accelerometer during operation at the first sampling rate against a plurality of threshold values;

determine that the first value of acceleration data corresponds to a first threshold value within the plurality the threshold values; and wherein the selection of the second sampling rate is based upon both the correspondence of the first value of acceleration data to the first threshold value and the classified activity category.

3. The non-transitory computer-readable medium of claim 2, wherein the accelerometer is a first accelerometer and the medium further comprises computer-executable instructions that when executed further perform at least:

selecting a second sensor that is not the first accelerometer to capture motion data from the user during performance of the activity based upon at least one of: (a) the correspondence of the first value of acceleration data to the first threshold value and (b) the classified activity category.

4. The non-transitory computer-readable medium of claim 3, wherein after selecting the second sensor, the first accelerometer and the second sensor are utilized to capture the user's movement.

5. The non-transitory computer-readable medium of claim 3, wherein the accelerometer is a first accelerometer and the medium further comprises computer-executable instructions that when executed further perform at least:

based upon selecting the second sensor, the first accelerometer is not used after the selection of the second sensor to capture the user's movement during the activity.

6. The non-transitory computer-readable medium of claim 2, wherein determining that the first sampling rate corresponds to the threshold value is configured to occur at a sampling rate processor located on the device and the determination of correspondence is further configured to be based upon at least one of: the first value of the acceleration data being equal to the first threshold value, the first value of the acceleration data being numerically closer to, and greater than, a second threshold value as compared to the threshold value, and the first value of the acceleration data is determined to be within a predefined range of the first threshold value.

7. The non-transitory computer-readable medium of claim 1, wherein the sampling rate processor is configured to determine the first sampling rate as a low-battery sampling rate corresponding to a low level of stored electrical energy in a power supply.

8. The non-transitory computer-readable medium of claim 1, wherein a first value of the acceleration data comprises at least one of an amplitude or a frequency.

9. The non-transitory computer-readable medium of claim 6, wherein the acceleration data corresponding to the classified activity category is configured to be stored at an analysis processor on the device, wherein the analysis processor is physically distinct from the sampling rate processor.

10. A unitary apparatus configured to be worn by a user, comprising:

a structure configured to be worn on an appendage of a user, comprising:

a power supply;

a sensor configured to capture acceleration data from the appendage of the user; and a non-transitory computer-readable medium comprising computer-executable instructions that when executed by at least one processor cause the at least one processor to perform at least:

receive the captured acceleration data at a sampling rate processor located on the unitary apparatus;

determine a first sampling rate, wherein the sampling rate processor is configured to select the first sampling rate with a value below an upper sampling rate in order to reduce power consumption by an analysis processor from the power supply during sampling;

sample the data captured by the sensor at the first sampling rate; and analyze the sampled data with the analysis processor in an attempt to classify the acceleration data into an activity category representing a sporting activity, recognized from a plurality of sporting activities, being performed by the user, wherein the sensor is a first accelerometer and the medium further comprises computer executable instructions that when executed further perform at least:

compare a value of acceleration data obtained from the accelerometer during its operation at the first sampling rate to a plurality of threshold values;

determining that the value of acceleration data corresponds to a first threshold value within the plurality the threshold values; and based upon the correspondence to the first threshold value and a classified activity category, selecting a second threshold value.

11. The unitary apparatus of claim 10, wherein the sampling rate processor is further configured to:
compare a value of the acceleration data to a threshold value; and
determine the first sampling rate as corresponding to the threshold value.

12. The unitary apparatus of claim 10, wherein the sampling rate processor is further configured to:
determine a second sampling rate corresponding to the activity category into which the acceleration data is classified, and in response to the determined second sampling rate, storing, by the analysis processor, acceleration data sampled at the second sampling rate.

13. The unitary apparatus of claim 12, wherein the second sampling rate corresponds to a low power consumption rate by the analysis processor that maintains a sampling resolution to capture data for the classified activity category.

14. A non-transitory computer-readable medium comprising computer-executable instructions that when executed by a processor is configured to perform at least:
a) receiving, from an accelerometer of a processor, acceleration data;
b) identifying sporting activity from a plurality of sporting activities based, at least in part, on the received acceleration data; and
c) adjusting a sampling rate of the accelerometer based on the sporting activity identified in b),
wherein the medium further comprises computer-executable instructions that when executed further perform at least:
comparing a first value of acceleration data obtained from the accelerometer during operation against a plurality of threshold values;
determining that the first value of acceleration data corresponds to a first threshold value within the plurality the threshold values; and
wherein the adjustment of the sampling rate is based upon the correspondence of the first value of acceleration data to the first threshold value,
wherein the accelerometer is a first accelerometer and the medium further comprises computer-executable instructions that when executed further perform at least:
comparing a value of acceleration data obtained from the first accelerometer during its operation at the sampling rate to a plurality of threshold values;
determining that the value of acceleration data corresponds to a first threshold value within the plurality the threshold values; and
based upon the correspondence to the first threshold value and a classified activity category, selecting a second threshold value.

15. The non-transitory computer-readable medium of claim 14, wherein the accelerometer is a first accelerometer and the medium further comprises computer-executable instructions that when executed further perform at least:
selecting a second sensor that is not the first accelerometer to capture motion data based upon the correspondence of the first value of acceleration data to the first threshold value.

16. The non-transitory computer-readable medium of claim 15, wherein after selecting of the second sensor, the first accelerometer and the second sensor are utilized to capture motion data.

17. The non-transitory computer-readable medium of claim 15, wherein the accelerometer is a first accelerometer and the medium further comprises computer-executable instructions that when executed further perform at least:
based upon selecting the second sensor, the first accelerometer is not used to capture motion data.

\* \* \* \* \*